United States Patent
Pierro, Jr. et al.

(10) Patent No.: US 6,625,570 B2
(45) Date of Patent: Sep. 23, 2003

(54) SYNCHRONOUS DETECTION AND REMOTE MONITORING AND REGULATING OF CELL POTENTIAL FOR CATHODIC PROTECTION

(76) Inventors: Joseph J. Pierro, Jr., RD 2 Box 316, Dayton, PA (US) 16222; Timothy B. Mullins, 5612 Aylsbro Ave., Pittsburgh, PA (US) 15217; James B. Sullivan, 130 Alderson Rd., Saxonburg, PA (US) 16056

( * ) Notice: Subject to any disclaimer, the term of this patent is extended or adjusted under 35 U.S.C. 154(b) by 107 days.

(21) Appl. No.: 09/883,794

(22) Filed: Jun. 18, 2001

(65) Prior Publication Data

US 2002/0008042 A1 Jan. 24, 2002

Related U.S. Application Data

(60) Provisional application No. 60/212,742, filed on Jun. 20, 2000.

(51) Int. Cl.⁷ .................................................. G06F 11/00
(52) U.S. Cl. .......................... 702/188; 702/89; 702/106; 361/18; 327/551
(58) Field of Search .......................... 702/188, 89, 106; 361/18; 327/551

(56) References Cited

U.S. PATENT DOCUMENTS

| | | | |
|---|---|---|---|
| 4,080,272 A | | 3/1978 | Ferry et al. |
| 4,351,703 A | | 9/1982 | Winslow, Jr. |
| 4,383,900 A | | 5/1983 | Garrett |
| 4,409,080 A | | 10/1983 | Slough |
| 4,998,208 A | | 3/1991 | Buhrow et al. |
| 5,216,370 A | | 6/1993 | Bushman et al. |
| 5,331,286 A | | 7/1994 | Rivola et al. |
| 5,390,237 A | * | 2/1995 | Hoffman et al. ......... 379/88.23 |
| 5,446,369 A | | 8/1995 | Byrne et al. |
| 5,642,461 A | * | 6/1997 | Lewis ....................... 388/812 |
| 5,785,842 A | | 7/1998 | Speck |
| 5,864,827 A | * | 1/1999 | Wilson ....................... 705/35 |
| 5,872,445 A | * | 2/1999 | Ozawa et al. ............. 320/137 |
| 6,128,755 A | * | 10/2000 | Bello et al. ............... 714/715 |

* cited by examiner

Primary Examiner—John Barlow
Assistant Examiner—Meagan S. Walling
(74) Attorney, Agent, or Firm—McKay & Associates, PC

(57) ABSTRACT

A system and method for regulating an adjustable DC supply and continuously and remotely monitoring measurements of reference cell potential and/or current for cathodic protection of a structure is disclosed. Cathodic protection devices use a logic circuit and/or microprocessor based monitor for removing identifiable components and noise from the system to arrive at the DC bias. A method is implemented herein to arrive at the true value of a reference cell potential measurement determined within a sample collection point or window calculated for the reference cell signal while the impressed current is still being applied. This measurement can be compared to a calculated shutdown and is communicated to a central computer accessible via a network such as the Internet. All output is automatically regulated and checked for target window accuracy using an automated voting scheme.

54 Claims, 15 Drawing Sheets

Independent Sync Signal Generation

Alternative Independent Sync Signal Generation

SHUTDOWN MEASUREMENT

VOTING SCHEME 60

REFERENCE CELL MODE - DC Supply Regulation and Volt Fault Detection

SYNCHRONOUS DETECTION AND REMOTE MONITORING AND REGULATING OF CELL POTENTIAL FOR CATHODIC PROTECTION

SPECIFIC REFERENCE

This application hereby claims benefit of filing date established by provisional application Ser. No. 60/212,742, filed Jun. 20, 2000.

BACKGROUND

1. Field of the Invention

The present invention relates generally to an electronic test set for measuring the IR free potential of a reference electrode with an impressed output applied. In particular, measured cell potential and/or current is continuously monitored using a micro-processor or logic circuit based, real-time data compilation means, and is automatically regulated using an auto-adjusting DC supply regulation means. Reference cell potential measurements free of distorting effects, residual components, and noise are periodically logged using communications boards, and the system can be remotely monitored and configured via telephone or over a network such as the World Wide Web (WWW).

2. Description of the Related Art

Cathodic protection impressed current is employed to prevent corrosion of metallic structures. Cathodic protection systems maintain a voltage potential between the structure and a ground reference cell. The National Association of Corrosion Engineers (NACE) has established, and industry has adopted, criteria with respect to measuring reference cell potential. The criteria provides for regulation of the upper and lower maximum allowable cell potentials for given applications. Specifically, industry has adopted a cell potential range of 850 millivolts to 1.2 volts DC for use in the protection of underground storage tanks and pipelines.

Maintenance of the correct impressed currents is very important. Inadequate cathodic protection may result from the cell potential falling below 850 millivolts. Conversely, cell potential above 1.2 volts may result in protective coatings separating from the structure.

Measuring reference cell potential and adjusting impressed current output requires the expertise of trained personnel, which is, in general, beyond the capabilities of many end users. This is partly due to the use of measurement systems employing the most economical means. A common technique used involves shutting off the impressed current and measuring cell potential as soon as possible thereafter. Known in the art then, this method requires a given amount of skill and relies upon the operator correctly interpreting measured results.

Traditionally, cathodic protection of structures is practiced through the use of impressed current. Occasionally an interface for controlling the current is provided between a rectifier and an external communications link. As an example, interfacing rectifiers to GPS units in order to perform a synchronous shutdown so that manual readings may be taken along a pipeline is practiced. See U.S. Pat. No. 5,785,842 (Speck), for example.

However, even a slight misinterpretation may result in a correspondingly incorrect adjustment of impressed current output. The need for interpretation of measured cell potential is due to cell potential decay, which begins immediately after impressed current is shut down. The rate of cell potential decay is a function of structure size and tank field polarization. In general, a small tank field will experience a more rapid decay in cell potential as opposed to a larger tank field.

As an example of error being induced in this manner, a technician taking measurements of cell potential just after impressed current shutdown may attempt to memorize the falling voltage reading approximately one to two seconds after shutdown. Because the decay is time-dependent, any deviation from a strict standard for interpretation compromises accuracy for the sake of economy.

One of the features of the present invention is to provide the end user with a continuous voltage readout of IR free cell potential with impressed current applied. These readings may be observed locally and/or remotely and must be free of distorting effects, residual components, and noise. Yet another feature allows the end user the ability to manually execute or program periodic execution of an impressed current shut down at which time a timer circuit will automatically activate and take multiple cell potential readings over a period of time, and thereafter compute, store, and display IR free cell potential. The manual shutdown serves two purposes: comparing shutdown cell potential results with the impressed current applied cell potential, and comparing the two readings for accuracy and for DC supply output adjustment.

Some rectifier manufacturers use circuitry that detects an upper and lower rectifier output. This circuit is often used in an attempt to correlate rectifier output and reference cell potential. The premise for this correlation is based on an assumption that there is a given degree of linear proportionality with respect to rectifier output verses reference cell potential. Using this technique, the rectifier output is adjusted to produce an upper allowable cell potential. The circuit is then adjusted to activate a light indicator or remote alarm. The above procedure is repeated for the lower allowable cell potential. Correlating rectifier output to reference cell potential compromises accuracy and requires the skills of trained technicians which is, in general, beyond the technical capabilities of most end users.

There is a need, then, for a continuously operable cathodic protection method and system that can automatically validate readings and automatically adjust output voltage to the structure, and which can monitor both current and reference cell potential measurements on-demand with real-time data display and compilation capabilities.

SUMMARY OF THE INVENTION

The objective of the present invention is to provide a system and method implemented therein for regulating output and continuously and remotely monitoring measurements of reference cell potential and/or current. Both reference cell potential and current is controlled using a logic circuit and/or microprocessor-based hardware system, and associated software, that monitors and logs cell potential readings and allows for remote monitoring of the readings via telephone and/or the Internet and/or other network compatible hand-held components. The cathodic protection device (CPD) automatically adjusts the DC supply's output providing the means for remotely maintaining cell potential within allowable operating limits. Yet another object of this invention is to provide an automatic electronic testing unit, which checks the proper operation of the cathodic protection impressed current system. Still a further object of this invention is to provide a system and method, which allows for a microprocessor-based shutdown at which time the CPD unit will automatically measure and store the cell potential readings, thereby maintaining a consistent shut-down interval with the measurement of the decay time being extrapolated. The stored measurements are then used for determining proper operation of both CPD and adjustable DC supply. Still another object of this invention is to provide a system that allows end users the means for the remote verification of proper operation and the means for system adjustment by personnel having minimum technical skills.

Therefore, a system and method is provided wherein a cathodic protection device operable in both current and reference cell modes, is adapted to vary output, which output is usually an adjustable DC supply. This output can correspond to either current or reference cell potential measurements that are optionally communicated to a central computer using internal interface units piggybacked on the cathodic protection devices. The voltage detection means, working in conjunction with each CPD, provides all measurements and inputs them to the central computer, wherein they are compared and cross-checked using a voting scheme means. This improves confidence in the measurements to meet target window regulation needs if the output must be varied or changed.

The system detects deviation from desired regulation occurring because of adjustable DC supply limitations, then flags and report such events. Also, the CPD uses a means of monitoring cell potential while the adjustable DC supply is operational, in which case real time data-compilation and monitoring is made possible by way of a reference cell potential monitor. This reference cell potential monitor can be logic circuit or micro-processor based. The monitor uses detection signal processing techniques to accurately derive the amplitude of the DC bias by removing identifiable components and noise such as distorting effects, signal minimum dips, and residual line frequency components. This DC bias is then correlated to the true reference cell potential measurement.

This system uses cathodic protection devices that further provide a means of measuring and calculating cell decay during an impressed current shutdown. This allows validation through a comparison of the calculated shutdown decay rate to a pre-entered estimate of structure decay rate, and then flags and reports errors. The system validates itself by using the best of a calculated shutdown decay rate or pre-entered decay rate to calculate time zero cell potential and compares it to the real time monitor value and flags and reports errors. The system can use central station software in conjunction with a user configurable web page for the purpose of making easily accessible reports available to operators and regulatory agencies concerning the operational history of an individual cathodic protection device or group of cathodic protection devices. The system can also use Internet addressing in conjunction with a telephone system, cell phone, radio links, or other Internet interfaces to access individual or groups of cathodic protection devices.

To arrive at a true reference cell potential measurement while impressed current is being applied to the structure, noise, distorting effects, and residual components such as a 50 or 60 Hz line component must be eliminated. The method generally comprises the steps of generating a sync signal and establishing a sample collection window for the sync signal so sample points of the reference cell signal are captured or acquired along minimums of the reference cell signal. As the signal is measured within this window, distorting effects such as an IR drop, and the small negative approaching dips on the leading edges of the minimums are removed. After then passing the sample points through a moving average filter, a residual component such as the 60 Hz component is removed and the DC bias is formed. This DC bias is then correlated to the true reference cell potential measurement.

The sample collection window is adjustable so at least one delay can be applied to the signal within the window at positions before and after the occurrence of the IR component and dips respectively. Using a simplified assumption, the delay may also be applied by determining a midway point on the at least one of the minimums of the reference cell signal such that there are no bounds on the window since only the time interval between falling and rising portions of the waveform is determined. The applied delays may further be calculated to account for phase lag introduced to the signal by a rectifier transformer supplying power to the structure.

Figure 1:
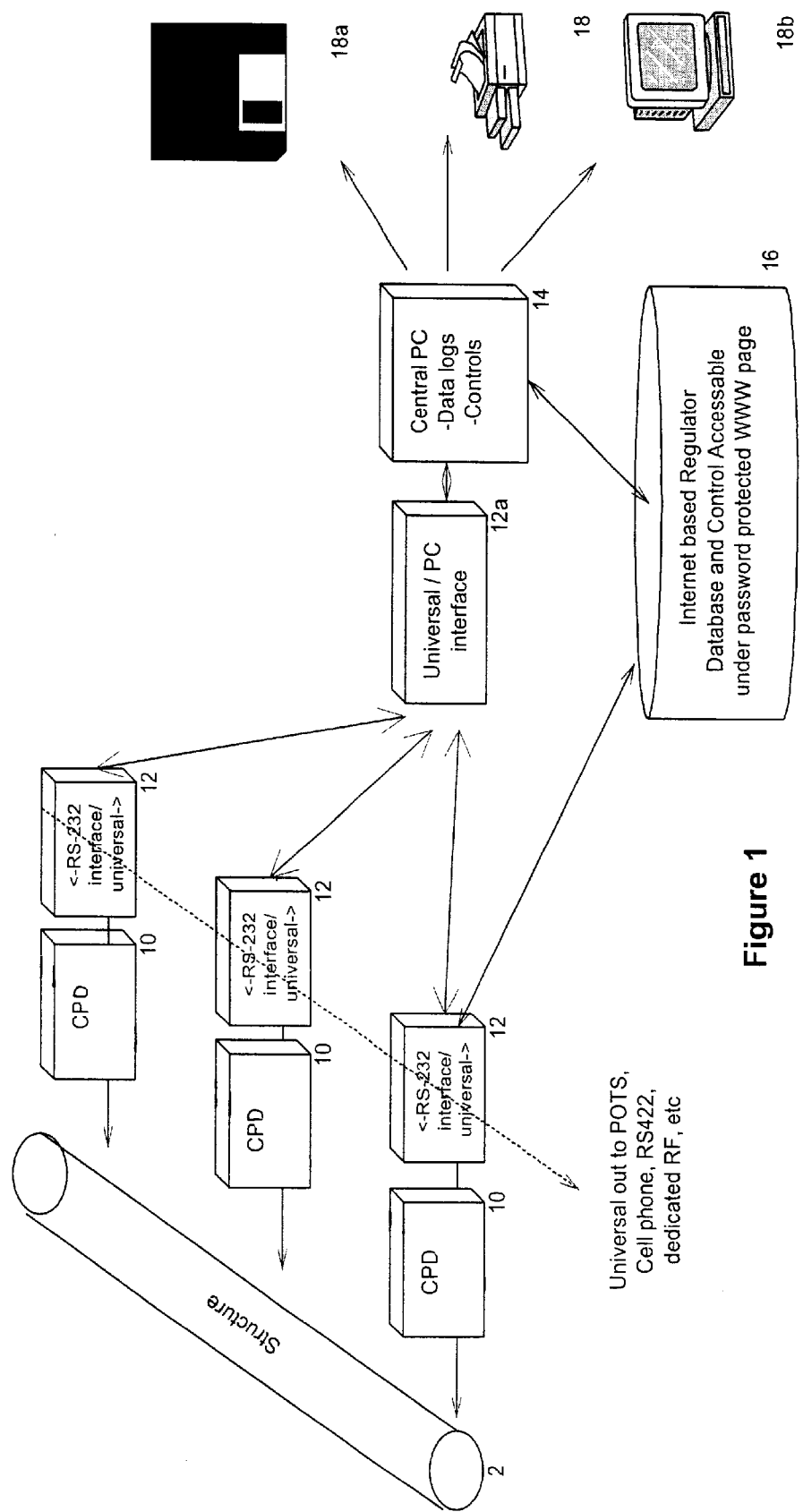
FIG. 1 is a top-level flow diagram showing the overall process wherein one or more cathodic protection devices communicate with a central PC running the central station software.

The flow diagrams are representative of software and logic flow that can be implemented in discrete circuits. It is, therefore, possible to configure discrete logic devices, and/or program a micro-processor based specialized device and/or a general-purpose computer to implement the invention, and the specification provides sufficient information to those skilled in the art to implement all functions of the invention in any such manner. The functions and/or devices are described using the detailed description wherein like reference numerals designate the same elements.

DETAILED DESCRIPTION OF THE PREFERRED EMBODIMENT

The system and method will now be described in detail in relation to a preferred embodiment and implementation thereof which is exemplary in nature and descriptively specific as disclosed. As is customary, it will be understood that no limitation of the scope of the invention is thereby intended. The invention encompasses such alterations and further modifications in the illustrated device, and such further applications of the principles of the invention illustrated herein, as would normally occur to persons skilled in the art to which the invention relates.

The top level diagram represented using FIG. 1 shows a series of one or more cathodic protection devices 10, each cathodic protection device 10 communicating with an internal interface unit 12 piggybacked on the cathodic protection device PCB via RS-232 or other suitable link. Each cathodic protection device (CPD) 10 is a box-like structure that contains within its interior at least a rectifier and an adjustable voltage scheme for adjusting and regulating a DC supply. Either further integrated therein or externally, a micro-processor or logic circuit based continuous monitor processes all signals to be communicated as further described. The internal interface units 12 are available with a variety of means to communicate externally including POTS (plain old telephone system), cell phone, dedicated radio links, RS-422, and other appropriate communication links. The CPD's incoming and/or outgoing address is adapted to become a phone number, a radio frequency, an Internet address, or the like.

Using these communication links, each cathodic protection device 10 plus interface 12 is accessible by a central station computer 14 running central station software and outfitted with appropriate link I/O 12a. Depending on the means chosen, the central station software could either communicate directly with each cathodic protection device 10 individually or as a group, or, alternatively, via an Internet addressing scheme 16, wherein all data is accessible over a network such as the Internet, or any intranet or digital network.

The central station computer 14 generally comprises an input device such as a mouse and/or a keyboard, and a display device such as a monitor. The computer also typically comprises a random access memory (RAM), a read only memory (ROM), a central processing unit (CPU), and a storage device such as a hard disk drive or a floppy drive.

The central station software on the central station computer (PC) 14 performs a number of roles. While cathodic protection devices 10 may be configured locally, the central station software serves as a means to remotely configure each cathodic protection device 10 with specific parameters. These configurable parameters include:

1) whether the unit is to regulate current which is applied directly or, alternatively, to use applied current to ensure derived reference cell potential falls within a target voltage range,
2) anticipated time constant for the system's shut-down decay rate,
3) periodic shut-down cycle time intervals,
4) adjustable DC supply upper and lower limits,
5) selection of data logging of events like applied voltage, applied current, derived cell potential, power outages, alarm occurrences, fault occurrences, and other monitored functions, and
6) a variety of selectable control and annunciation schemes.

The software is able to co-ordinate a simultaneous shut-down of cathodic protection devices 10, an action useful for deriving cell potential readings on a structure protected by multiple cathodic protection devices 10 as is the case with the protection of a pipeline or other large structures.

The software is further able to query individual cathodic protection devices 10 at user set intervals or respond to cathodic protection device 10 initiated communication. This query and communication ability is used to compile a historical database of the operation of the cathodic protection device 10 including applied voltage, applied current, derived cell potential, power outages, alarm occurrences, fault occurrences, and other monitored functions. The software communication further can allow a notification of whether or not the central station of the cathodic protection device 10 is operating outside of desired parameters. It is further capable of acting as a convenient interface 12a for keeping track of multiple groups of cathodic protection device 10 sites by means of incorporating site maps and drawing tools.

The software is also able to assemble cathodic protection device data into a form that is accessible by owners of the system and central station software so they may generate hardcopies 18, e-mail files 18a, or web page reports 18b. These can be posted to a user configurable web page so that interested regulatory agencies or authorized third parties, with appropriate password access, can examine any particular cathodic protection device's operational history at any time via the Internet addressing scheme 16. Thus, the software serves as an interface between the Internet 16 and the central station PC 14, thereby allowing users to password access cathodic protection device configurations, query features, and report functions available on the central station PC 14.

Figure 2:
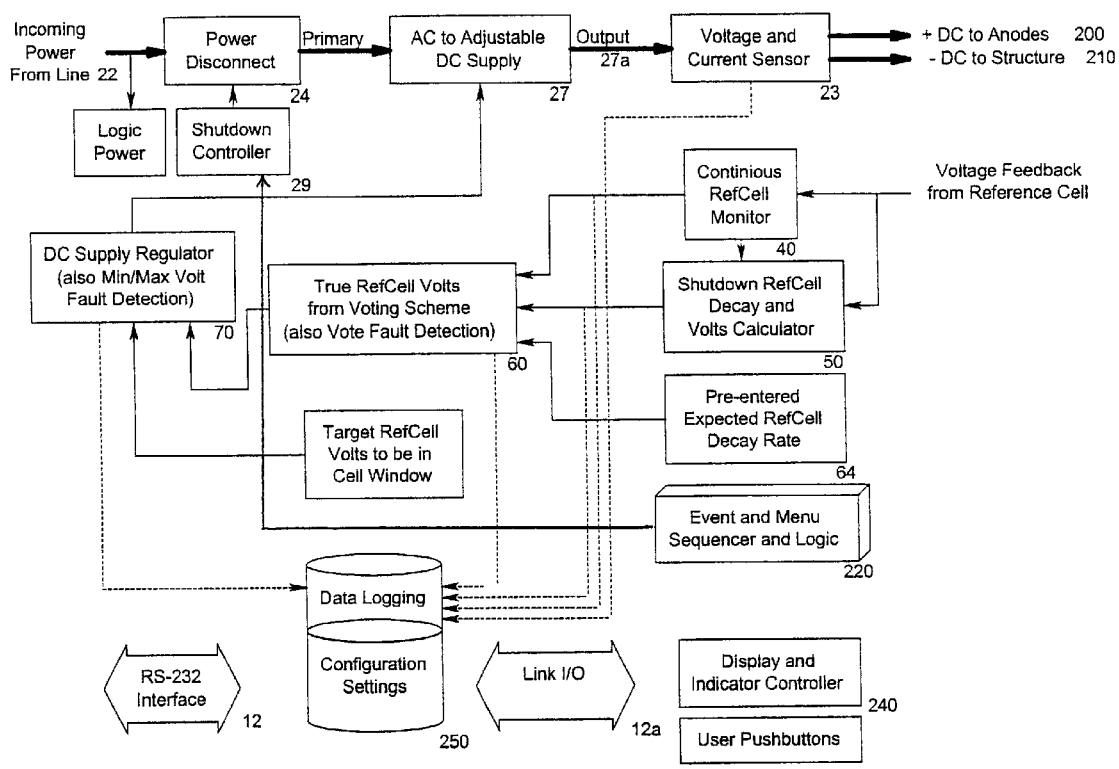
FIG. 2 is a flow diagram showing the cathodic protection device functioning in reference cell regulation mode.

Referencing FIG. 2, the cathodic protection device 10 is represented here functioning in reference cell potential regulation mode. Each CPD 10 is configurable to regulate either current or reference cell potential by means of varying output provided from an adjustable DC supply 27. In reference cell potential regulation mode, once AC line power 22 is provided to logic circuits, it is routed through a logic controllable power disconnect 24 that is used when sequencing a shutdown. Though shown as a primary power disconnect for a transformer, this disconnect function could simply be placed elsewhere, for example by shutting down gating on a variable voltage or pulse DC supply. Primary power 22 then goes into an adjustable DC supply 27, which has course upper and lower limits that define a regulation or adjustment window which are set in the field, but which has fine adjustments within that window set by the DC supply regulator 70. DC power 27a is then passed through a voltage and current sensing section 23. Positive power is then passed to either one or a series of external anodes 200. Negative power is passed to the structure 210 being protected. The structure 210 as defined herein may be any underground conduit or storage tank, or any other structure that may potentially be subjected to corrosive environments.

The shutdown controller 29 is controlled by the event and logic sequencer 220. It uses a switching device to stop the adjustable DC supply 27 from delivering power to the structure 2. It does not shutdown power to the cathodic protection device 10 logic circuits and need not necessarily appear on the input to the adjustable DC power supply.

The adjustable DC supply 27 has an upper and lower limit that defines an adjustment window. This is so as to limit the range of voltage output of the adjustable DC supply 27 that is under control of event and logic sequencer 220 so that if there was a logic error, excessive voltage and current could not be passed to the structure 2. At installation, the appropriate adjustment window is set by the installer so that the adjustable DC supply 27 is able to provide a suitable range of voltages necessary to protect the structure 2 as called for by DC supply regulator 70. The adjustable DC supply 27 can use a variety of devices and methods to vary the effective output voltage being applied to the structure 2.

One method is to use SCRs, IGBTs, MOSFETs or other type of regulation device to regulate the level of a DC voltage being applied in accordance with that required by the DC supply regulator 70.

Another method is to use SCRs, IGBTs, MOSFETs or other type of switching device to regulate frequency, duration, and/or amplitude of a series of DC pulses in order to regulate the effective DC voltage being applied in accordance with that required by the DC supply regulator.

Figure 2A:
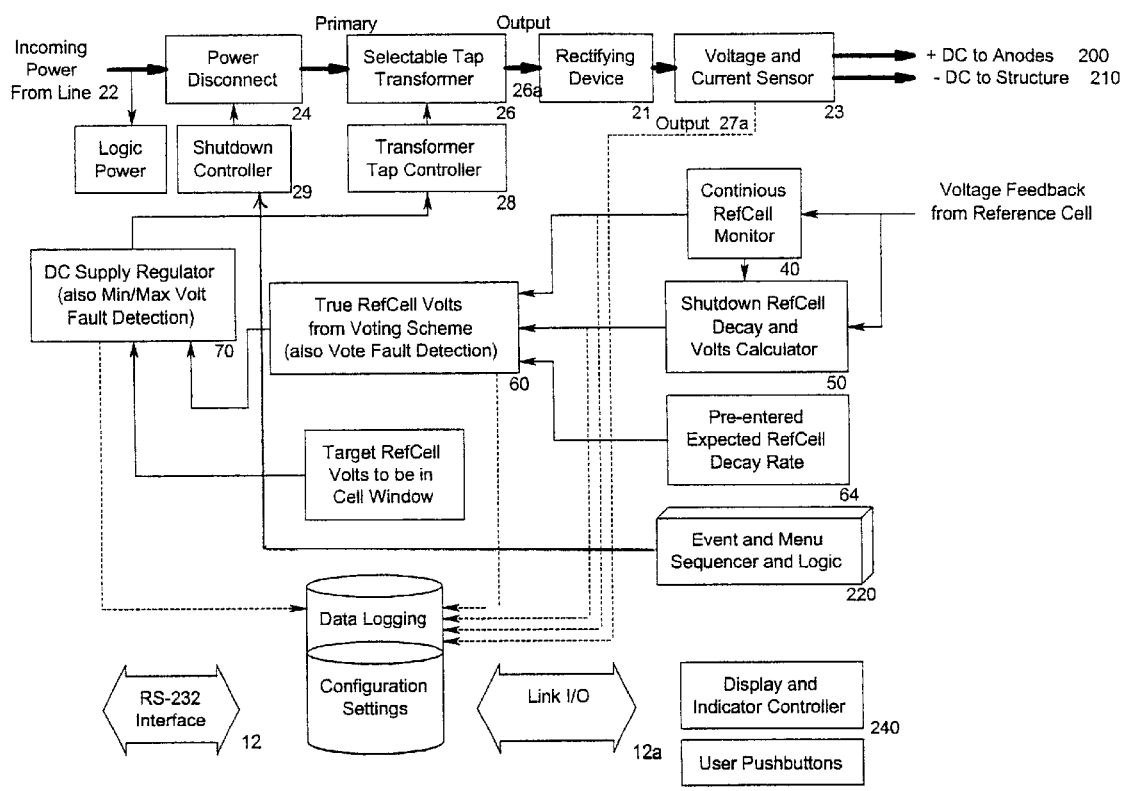
FIG. 2a is a flow diagram showing the cathodic protection device functioning in reference cell regulation mode with an adjustable DC supply comprised of an adjustable tap transformer, transformer tap controller, and rectifying device.

Another is to use a variable output transformer coupled with a rectifying device, a form of which is depicted in FIG. 2a.

The adjustable DC supply's output 27a is set by the DC Supply regulator 70 which in turn acts to keep the true reference cell potential 60 within the target window. This regulation scheme is detailed by FIG. 7.

The voltage and current sensor section 23 uses as a preferred means of voltage detection, voltage divider resistors to reduce the adjustable DC supply output to a level suitable for introduction to logic circuitry. The divided voltage is then averaged by a low pass filter and used as a proxy for the adjustable DC supply's voltage output 27a for display 240 and data logging 250 purposes. The voltage and current sensor section 23 also uses a low pass filtered output voltage of a current sense device, which may be a hall effect device, shunt, or a current sense resistor that is placed in series with power flow in order to provide voltage as a proxy for impressed current being delivered to the structure 2 (FIG. 1).

Referencing FIG. 2a, the cathodic protection device 10 is shown in reference cell potential regulation mode. The only difference between the logic circuitry of FIG. 2 and FIG. 2a is the adjustable DC supply 27 (FIG. 1) is shown as comprised of a selectable tap transformer 26, a rectifying device 21, and a transformer tap controller 28.

As in FIG. 2, incoming AC line power 22 is applied to logic circuits, through a logic controllable power disconnect 24, which is controlled by the shutdown controller 29, and the event and logic sequencer 220 acting in series.

Through the power disconnect 24, power is then fed into selectable tap transformer 26, which has course taps set in the field but which has fine taps that are set by the transformer tap controller 28. The selectable tap transformer output 26a, which has a voltage level determined by the settings of the course and fine taps, is then passed into a rectifying device 21 of suitable power rating.

Then, as demonstrated in FIG. 2, DC power output 27a is passed through a voltage and current sensing section 23. Positive DC voltage is applied to either one or a series of external anodes 200. Negative DC voltage is passed to the structure being protected 2.

Figure 18:
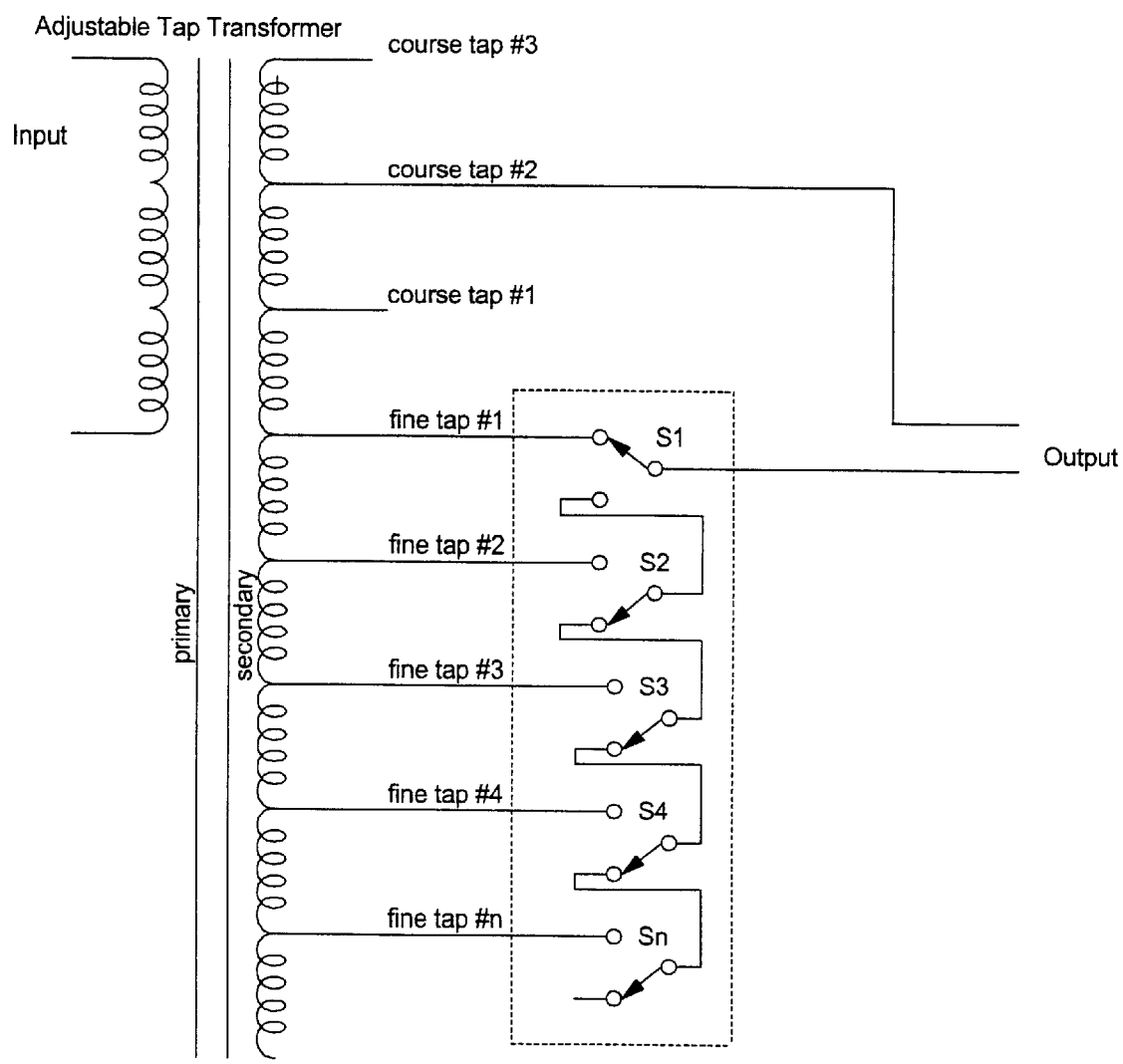
FIG. 18 is a flow diagram showing detail on the transformer tap controller.

The selectable tap transformer 26 has a series of course secondary taps and a series of fine secondary taps (FIG. 18). In general, voltage output of the selectable tap transformer 26 can be made incrementally higher by selecting correspondingly higher taps. A change in course tap settings impacts output voltage over a greater range than does a change in fine tap settings. There is a series of switching devices connected to the selectable tap transformer's 26 fine taps that constitutes the transformer tap controller 28, for which detail is provided in FIG. 9. The transformer tap controller 28 does not control course tap settings. This is meant to limit the range of voltage output of the selectable tap transformer 26 that is under control of event and logic sequencer 220 so that if there was a logic error, excessive voltage and current could not be passed to the structure 2. At installation, the appropriate course tap setting is set by the installer so that the selectable tap transformer 26 is made to provide a suitable range of voltages by having the transformer tap controller 28 adjust the fine tap settings.

The adjustable tap transformer output 26a is controlled by the transformer tap controller 28, which in turn is controlled by the DC Supply regulator 70 which in turn acts to keep the true reference cell potential 60 within the target window. This regulation scheme is further detailed with reference to FIG. 7a.

Figure 3:
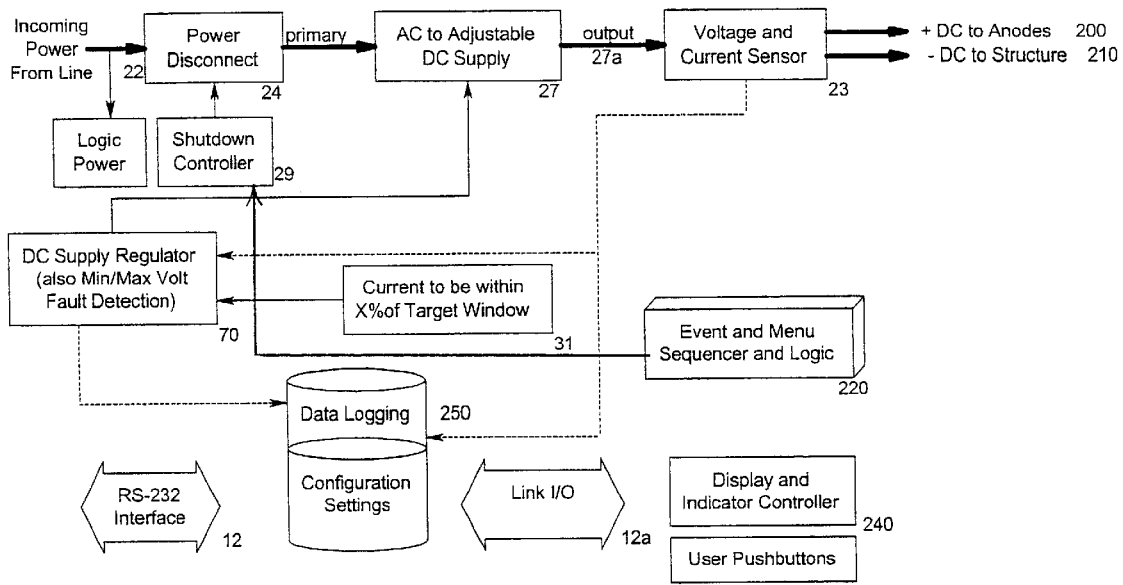
FIG. 3 is a flow diagram showing the cathodic protection device functioning in current regulation mode.

FIG. 3 shows the cathodic protection device 10 in current regulation mode. The main difference between this mode and the reference cell mode depicted in FIG. 2 is that the cathodic protection device 10 monitors current being applied to the structure 2 instead of monitoring reference cell potential.

As in FIG. 2, once incoming power from the AC line 22 is provided to logic circuits, it is routed through a logic controllable power disconnect 24 (which may appear elsewhere), which is controlled by the shutdown controller 29 which is controlled by the event and logic sequencer 220. After the disconnect 24, power is then fed into an adjustable DC supply 27, then through a voltage and current sensing section 23. Positive power is then passed to external anodes 200. Negative power is passed to the structure 2. The adjustable DC supply 27 has an upper and lower limit that defines an adjustment window.

In the current regulation mode, the adjustable DC supply's output 27a is set by the DC supply regulator 70 which in turn acts to keep the current being applied to the structure 2 within a target window 31. This regulation scheme is detailed by FIG. 8.

Figure 3A:
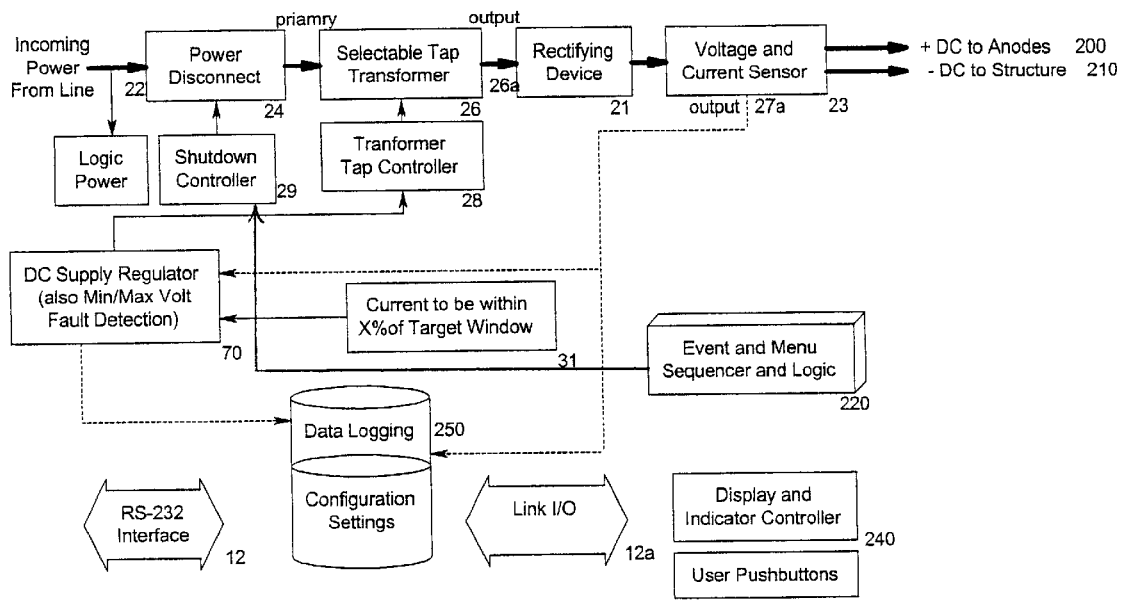
FIG. 3a is a flow diagram showing the cathodic protection device functioning in current regulation mode with an adjustable DC supply comprised of adjustable tap transformer, transformer tap controller, and rectifying device.

Referencing FIG. 3a, the cathodic protection device 10 is shown in current regulation mode. The only difference between FIG. 3 and FIG. 3a is the adjustable DC supply 27 is shown as comprised of a selectable tap transformer 26, a rectifying device 21, and a transformer tap controller 28.

As in FIG. 3, after the AC line 22 is provided to logic circuits, it is routed through a logic controllable power disconnect 24, which is controlled by the shutdown controller 29, which is further controlled by the event sequencer 220.

After the disconnect 24, power is then fed into a selectable tap transformer 26 as previously described in FIG. 2a, then into a rectifying device 21. The adjustable tap transformer output 26a is controlled by the transformer tap controller 28, which in turn is controlled by the DC supply regulator 70 which in turn acts to keep the current being applied to the structure 2 within a target window 31. This regulation scheme is detailed by FIG. 8a. Then, as in FIG. 3, DC power 27a is then fed to a voltage and current sensing section 23. Positive power is then passed to external anodes 200. Negative power is passed to the structure 2 being protected.

The reference cell continuous monitor 40 (FIGS. 2 & 2a) is logic circuit arrangement or a micro-processor based device capable of providing continuous measurements of reference cell potential regardless of whether or not the cathodic protection device system has been shutdown. It can provide reference cell potential readings while impressed current is being applied to the structure. The reference cell continuous monitor 40 can be an on-board device adapted to operate in conjunction with the cathodic protection device system with an integral reference cell, or as a separate, portable, possibly battery operated monitor in conjunction with a portable reference cell.

Figure 4:
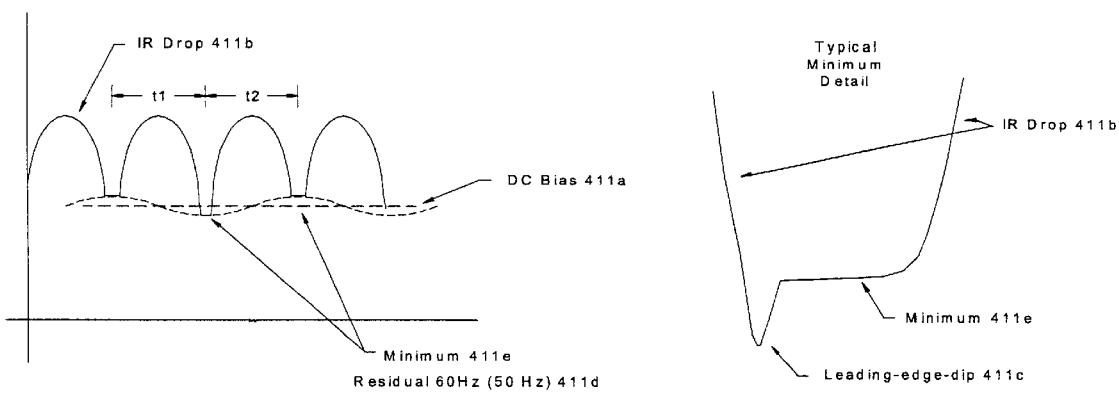
FIG. 4 is a flow diagram illustrating a typical profile for a reference cell signal.

As represented using FIG. 4, in the case where fully rectified 60 Hz, or where fully rectified 50 Hz or where pulsed width, height, or frequency controlled DC is being applied to protect the structure (which is dependent upon line frequency and/or rectification scheme used), a typical reference cell signal 411 from the reference cell input usually is comprised of four clearly identifiable components along with other various forms of noise like RF. These components include the signal itself, which is a constant DC level or bias 411a on the reference cell signal 411, and which alone represents the component of interest as it correlates with true residual DC reference cell potential, and the distorting effects and residual components below:

1) a 120 Hz (or 100 Hz or pulsed DC) varying DC component from the full wave rectified 60 Hz (or 50 Hz or pulsed DC) being applied by the cathodic protection device to the protected structure and this is often referred to as the IR drop 411b,
2) a component that appears as relatively small negative going dips 411c on the leading edges of the reference cell signal's minimums 411e,
3) a non-rectified residual line frequency (60 Hz [or 50 Hz]) component 411d often with a phase delay which usually originates from the surrounding power grid.

To arrive at an amplitude for the DC bias 411a on the reference cell signal, which is the component of interest as it correlates with the reference cell potential, the three identifiable residual components/distorting effects and any noise like RF must be removed.

To accomplish this, the reference cell signal 411 is fed into a minimum detector, which detects the periodic minimums 411e (negative to positive slope reversals) that occur on the reference cell signal 411. Note the amplitude of these minimums 411e would represent the residual DC bias 411a that correlates with the reference cell potential were it not for the remaining leading-edge dips and the residual 60 Hz (50 Hz) 411d components.

As a first step in detecting minimums 411e on the reference cell signal 411, either a dependent sync reference signal (derived from the reference cell signal itself) or an independent sync reference signal (derived from the AC line or the pulsed DC rate, suitable for integral monitor/rectifier applications) is fed into a detector with the intention of generating a 120 Hz, 100 Hz, or pulsed DC pulse train to serve as a sync signal 45 used in sampling the periodic minimums 411e on the reference cell signal 411 itself. Note that the dependent schemes for sync signal generation, in addition to being applied to the reference cell signal as described below, could also be applied to an independent sync signal like the line (pulsed DC) signal, thereby making them useable for independent sync signal generation as well. Also note that when a 120 Hz (100 Hz or pulsed DC) IR component 411b has an out of phase residual 60 Hz (50 Hz) component 411d superimposed upon it, schemes that use sync detection plus a delay to predict reference cell minimums may require adaptive methods like alternating between two delays.

Figure 5:
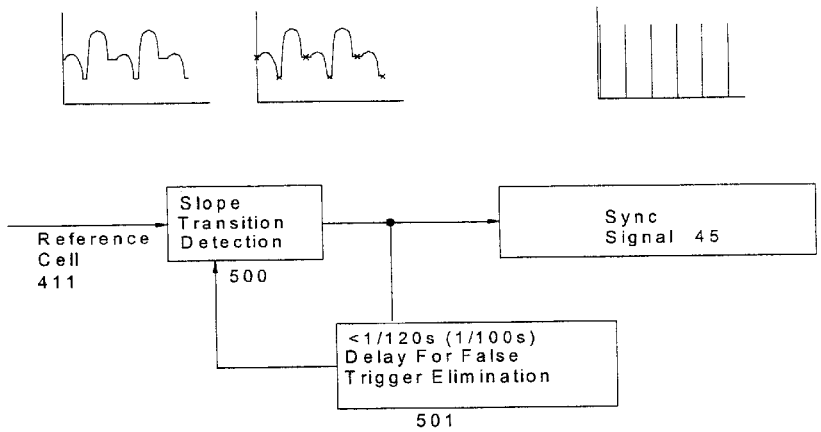
FIG. 5 depicts a method of generating a sync signal from the reference cell signal used as part of a scheme for deriving reference cell potential while impressed current is being applied to the structure.

One method of dependent sync signal generation, see FIG. 5, is to use a detection signal processing method (either analog or digital) to detect a point of particular slope transition (either a minimum, maximum, or inflection) 500 on the reference cell signal 411. This slope transition 500 is to occur within a time window following the preceding detection of a similar slope transition by approximately $\frac{1}{120}$ sec ($\frac{1}{100}$ sec) 501. This is the expected time between like-slope transitions on a 120 Hz (100 Hz) impressed waveform. A frequency measuring scheme like a phase lock loop can be employed to dynamically position this window for adaptive detection, required where pulsed DC is used because pulses are not necessarily at 120 Hz (100 Hz) intervals. These like-slope transition events are then used to generate a sync signal 45 to which a delay is applied 49 (FIG. 9) as necessary to account for having detected like-slope transitions rather than occurrence of the true 120 Hz (100 Hz or pulsed DC) minimums 411e on the original reference cell signal 411. Note the sample collection window must be of sufficient duration to capture slope changes and is employed to eliminate false like-slope transitions outside the expected time frame. Also, note that window placement may need to be alternately adjusted and/or it's width expanded so as to properly capture like-slope transitions in situations where an out of phase residual 60 Hz (50 Hz) signal 411d is impressed upon a 120 Hz (100 Hz) IR signal 411b. In this manner, adjacent like-slope transitions alternate between a value greater than and less than $\frac{1}{120}$ sec ($\frac{1}{100}$ sec), though the closer the like-slope transitions are to the regularly spaced minimums, the smaller this alteration will be.

Figure 6:
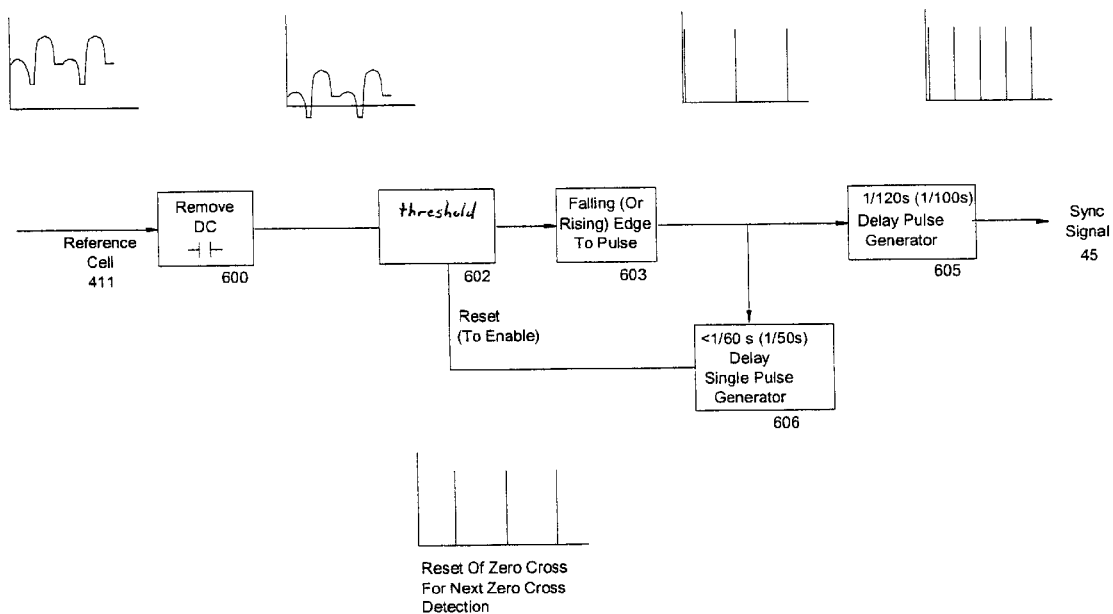
FIG. 6 depicts an alternate method of generating a sync signal from the reference cell signal used as part of a scheme for deriving reference cell potential while impressed current is being applied to the structure using a duplicated reference cell signal having all DC components stripped therefrom.

Another method of dependent sync generation, FIG. 6, uses a detection signal processing method (either digital or analog) that first removes all DC components 600 from a duplicated reference cell signal 412. This shifts downward the duplicate reference cell signal 412 that it periodically crosses a zero volt threshold 602. The DC components 600 could be left in the duplicate reference cell signal 412 and/or the threshold 602 could be established at some positive value, but this zero-cross illustration is chosen for simplicity. Each time the DC-free duplicate reference cell signal crosses the threshold 602 in a falling, negative sloping direction 603 (or in a rising, positive sloping direction, but not both), expected to occur at a 120 Hz (100 Hz or pulsed DC) rate, the events generate a sync signal 45. The sync signal 45 may then have applied a delay 49 to account for having detected the voltage threshold-cross on the DC-free duplicate reference cell signal 412 rather than occurrence of the true 120 Hz (100 Hz or pulsed DC) minimum 411e on the original reference cell signal 411. Note as in the prior method, by knowing the threshold-crosses are expected approximately $\frac{1}{120}$ sec ($\frac{1}{100}$ sec or pulse) apart, false triggers can be avoided by establishing a sample collection window. Also note as in the prior method, window placement may need to alternately adjusted and/or it's width expanded so as to properly capture threshold-crosses in situations where an out of phase residual 60 Hz (50 Hz) signal 411d is impressed upon a 120 Hz (100 Hz) IR signal 411b.

A problem can occur with this threshold-cross detection method when applied to a reference cell signal with a significant residual 60 Hz (50 Hz) component 411d. It is possible that with significant residual 60 Hz (50 Hz) components, the duplicate DC-free reference cell signal will only cross the voltage threshold at a half the 120 Hz (100 Hz or pulse DC) rate rather than at the full 120 Hz (100 Hz or pulsed DC) rate.

To correct for this, the first time the duplicate DC-free reference cell signal crosses the threshold 602 in the downward direction (or in the upward direction, but not both), the event generates a sync pulse 603. Then, with the detection scheme disabled, the next threshold-cross expected $\frac{1}{120}$ sec ($\frac{1}{100}$ sec) later is not detected, but is predicted to be $\frac{1}{120}$ sec ($\frac{1}{100}$ sec) later than the threshold-cross just detected and a sync pulse is generated at that delay point 605. Then, the detection scheme is re-enabled before the next threshold-cross, which is expected at about $\frac{1}{60}$ sec ($\frac{1}{50}$ sec) later than the preceding detection and a sync pulse is generated 606 upon detection. Thus, every other 120 Hz (100 Hz or group of pulsed DC) threshold-cross would be detected and the time of the threshold-cross in between would be predicted to be $\frac{1}{120}$ sec ($\frac{1}{100}$ sec) later than those threshold-crosses detected thereby filling in what would otherwise be gaps. Note this method of generating a sync pulse $\frac{1}{120}$ sec ($\frac{1}{100}$ sec) after detection to fill in gaps may increase inaccuracy as the residual 60 Hz (50 Hz) signal 411d is phase shifted from the 120 Hz (100 Hz) IR component 411b. As before, the sync signal 45 may have applied a delay 49 (FIG. 9) to account for having detected the voltage threshold-crosses on the DC-free duplicate reference cell signal 412 rather than occurrence of the true 120 Hz (100 Hz or pulsed DC) minimums 411e. As in the previous dependent sync signal generation method, a frequency measuring scheme like a phase lock loop can be applied with this method too to adapt it for pulsed DC to assist in filling a consecutive series of threshold-cross gaps introduced by residual 60 Hz (50 Hz) signals.

Figure 7:
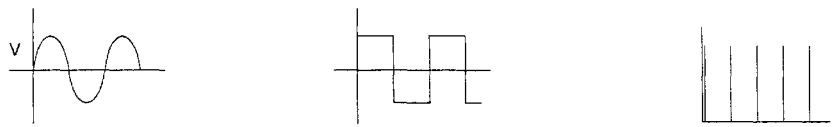
FIG. 7 depicts a method of generating a sync signal from an independent reference cell signal used as part of a scheme for capturing values of reference cell minimums.

One method of independent sync signal generation, FIG. 7, can be accomplished with a non-rectified AC line 42 (or pulsed DC 41) reference signal analyzed by a slope detection algorithm hunting for maximum positive and negative slope events (or alternatively zero slope or peak events), that is, where the reference signal crosses the zero volt axis 700 (or alternatively where it is maximally distant from the zero axis). Note a dependent sync is valid because the AC line reference signal generating the sync is correlated with reference cell minimums since the same AC is being rectified and applied to the structure (or the same variable AC is being used to control pulsed DC to the structure). As a specific example of a detector for maximum positive and negative slope events, a software or hardware comparitor can be used to compare the reference signal to a zero volt axis 700 (or arbitrary voltage level if a bias has been added to the reference signal) thereby generating rising and falling sync edges corresponding to rising and falling threshold crossing events on the reference signal. Then, an edge to pulse generator 701 is employed to convert both rising and falling edges to a sync signal 45. As before, the sync signal 45 may have applied a delay 49 to account for having detected the voltage threshold-crosses on the DC-free duplicate reference cell signal 412 rather than occurrence of the true 120 Hz (100 Hz or pulsed DC) minimums 411e. A DC bias can be added to the reference signal to assure positive only voltages if necessary to simplify introduction to signal processing hardware.

Figure 8:
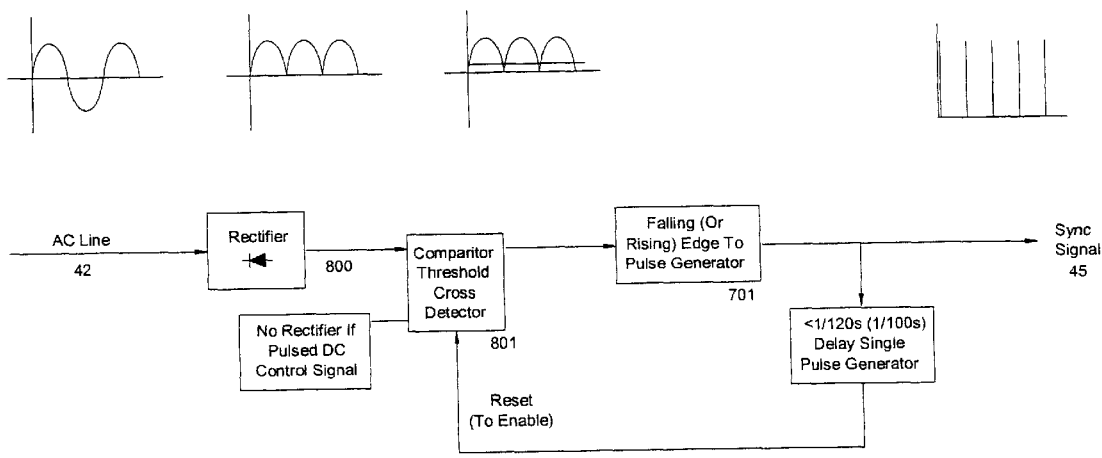
FIG. 8 depicts an alternate method of generating a sync signal from an independent reference cell signal used as part of a scheme for deriving reference cell potential while impressed current is being applied to the structure.

Another method of independent sync generation, FIG. 8, is to strip the AC line reference signal 42 of any DC component and feed it into a full wave rectifying device 800 (these steps are not required for pulsed DC). This rectified signal is then fed into a threshold-cross detector 801, which monitors a threshold above zero. Then, each time the reference signal crosses the volt threshold in a falling, negative sloping direction (or in a rising, positive sloping direction but not both), which is expected to occur at a 120 Hz (100 Hz or pulsed DC) 411b, the pulses are generated 45. Note as before any small delay in hitting the true reference signal minimum as introduced by a near zero threshold can be compensated for by adding a delay 49 to the sync signal 45.

So as noted above and now with further reference to FIG. 9, with the generation of the sync pulses 45, the next step is to apply a suitable delay 49 to them so that they can guide a sample/hold section 420 in capturing samples during minimums 411e on the reference cell signal 411 devoid of the small negative going dips 411c on the leading edges of the minimums 411e and devoid of distorting effects of the 120 Hz (100 Hz or pulsed DC) IR drop component 411b.

Figure 9:
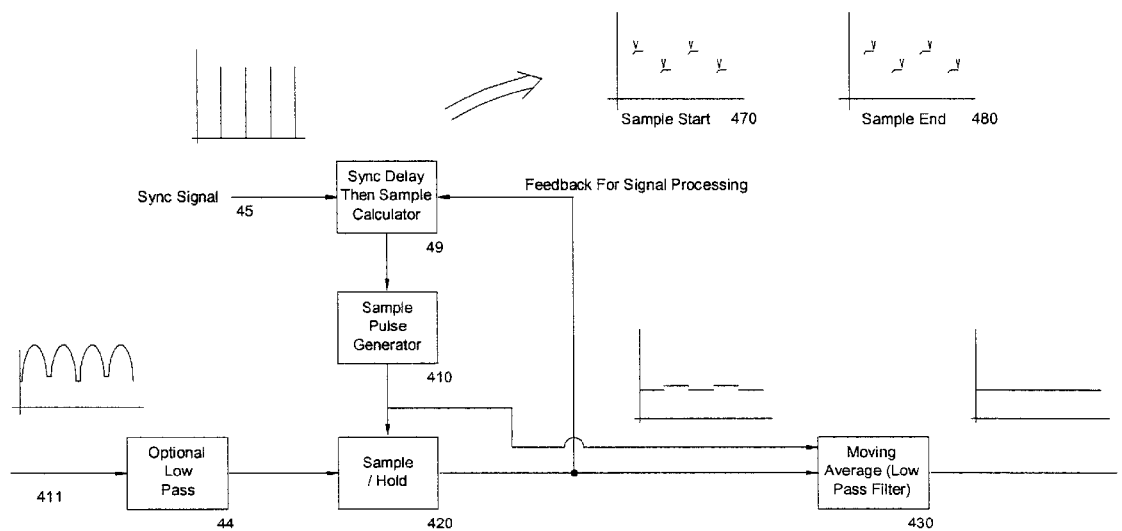
FIG. 9 depicts a method of deriving a reference cell potential measurement while impressed current is being applied to the structure.

FIG. 9 shows the method for establishing a sample collection window within which measurements of the reference cell signal 411 are taken. The sample window duration is dynamically adjusted by the sync delay then sample calculator 49, and is defined as the interval between the sample start delay 470 and the sample end delay 480. The sync delay then sample calculator 49 is intended to allow capture of a subset of reference cell signal minimums 411e devoid of the small negative going dips 411c on the leading edges of the minimums 411e and devoid of distorting effects of the 120 Hz (or 100 Hz or pulsed DC) IR drop component 411b. The sync delay then sample calculator 49 may be configured to collect multiple samples during each reference cell cycles and/or take single samples of each reference cell cycle, but varies each sample slightly in timing so as to capture the average profile of the sample collection window over many cycles. The sample window may necessarily include portions of the small negative going dips 411c on the leading edges of the minimums 411e and distorting effects of the 120 Hz (or 100 Hz or pulsed DC) IR drop component 411b as a part of the process of identifying and tracking their bounds. However, once their bounds are identified, a subset of samples devoid of their effects would be used to determine reference cell potential.

The sync delay then sample calculator 49 begins with an initial pre-set, field adjustable base delay. In the case of using an independently generated sync signal from the AC line 42, this initial base delay is for the most part a function of the phase lag between the AC line 42 and the rectified current applied to protect the structure 2 (i.e. the base delay is primarily from rectifier transformer lag when one is being used). In the case of using a dependent sync signal, that generated from the reference cell itself, an initial base delay, when required, would depend on the detection method generating the sync signal 45.

Using signal processing techniques applied to feedback from the minimum 411e sample/hold section 420, the sync delay then sample calculator 49 will incrementally add to or subtract from the base delay in order to establish sample start delay 470 and sample end delay 480 bounds. The sample start delay 470 is hunted so it is positioned after the leading-edge-dip component 411c from the reference cell signal 411. The sample end delay 480 is hunted so it is positioned before the distorting effects of the 120 Hz (100 Hz or pulsed DC) IR drop component 411b returns. Next, the sync delay then sample calculator 49 will systematically position samples (one per minimum 411e or optionally a cluster at a minimum 411e) between the sample start delay 470 and sample end delay 480 bounds, adjusting the bounds dynamically when required. By drawing samples from between the sample start delay 470 and end delay 480, a profile of the region of interest in the reference cell signal's minimum 411e emerges. Note in situations where an out of phase residual 60 Hz (50 Hz) signal 411d is impressed upon a 120 Hz (100 Hz) IR signal 411b, the sample start delay 470 and the sample end delay 480 may each tend to have two alternating distinct values. This arises because the sync signal 45 are often equally spaced whereas the alternating shifted reference cell minimums 411e will not be. However, the average of the pair of alternating start delays 470 and the average of the pair of alternating end delays 480 may often be used without a material effect on accuracy. Accuracy will be a function of the 60 Hz (50 Hz) 411d phase delay relative to the IR signal 411b together with the amplitude of IR drop 411b and the 60 Hz (50 Hz) 411d amplitude.

One signal processing method for determining the sync delay then sample calculator's 49 sample start delay 470 is to track the slope of reference cell signal 411 after the base delay and, once the slope's value and rate of change reach pre-set values, the dip 411c is deemed to have concluded and the ideal sample start delay bound determined. Typical durations for leading-edge-dips 411c have been arrived at empirically for a variety of installations and the calculated value can be verified and adjusted in light of these measurements.

One signal processing method for determining the sync delay then sample calculator's 49 sample end delay 480 is to track the slope of the reference cell signal 411 after the sample start delay 470 and once the slope's value and rate of change reach values that indicate presence of the distorting effects of the 120 Hz (100 Hz or pulsed DC) IR drop component 411b, set that point as the ideal sample end delay 480.

Figure 10:
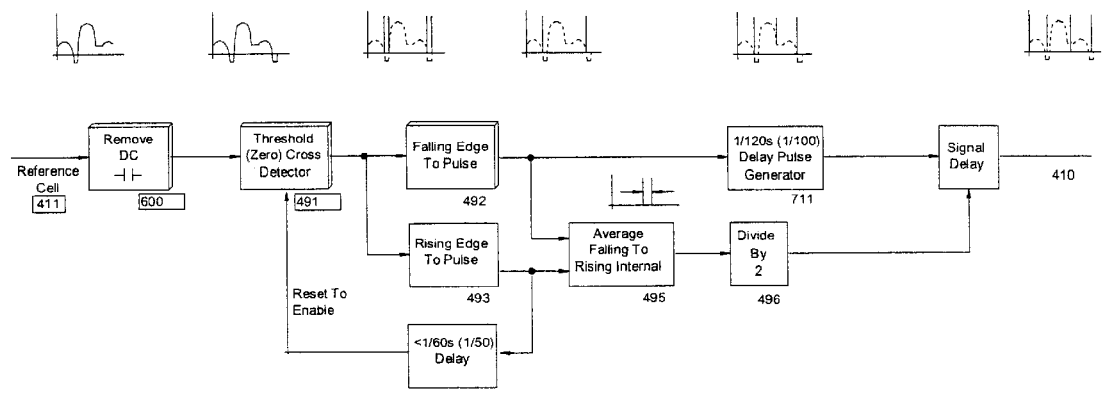
FIG. 10 depicts a minimalist integral rectifier/monitor scheme of deriving the reference cell potential measurement while impressed current is being applied to the structure, wherein the sample collection window is established in a simplified manner.

An alternate method of determining the sample start delay 470 and sample end delay 480, see FIG. 10, entails two simplifications and is applicable when generating a dependent sync signal using a reference cell potential threshold-cross detector method 491 (or when augmenting an independent sync signal with a signal using a reference cell potential threshold-cross method). Note for simplicity the threshold is shown here at zero volts though it could be set to another value. First, rather than a sample start delay 470 and a sample end delay 480 defining a window having a range, there is only a single delay 410 applied to the sync signal 45 such that the sample collection window is singular. A point sample (or cluster of samples to resolve a point given noise and errors) is then taken after a signal delay 410 by the sample/hold section 420. This signal delay 410 is not computed using signal processing techniques, but rather by adjusting this delay 410 so that a sample is taken midway along the reference cell minimum 411e. The simplifying assumption here is this midway point will occur after the leading edge dips 411c and before the distorting effects of the 120 Hz (100 Hz or pulsed DC) 411b. To determine the midway point on the reference cell minimum 411e, the width of the reference cell waveform when it crosses the voltage threshold 491 is determined. In other words, the time interval 495 between the falling portion 492 and rising portion 493 of the reference cell waveform is determined. Then, a delay of half this interval 496 is applied to the sync signal 45. Note as outlined previously in the section on dependent sync signal generation, where only every other reference cell minimum 411e is expected to cross the fixed voltage threshold 491 as can be the case with superimposed 60 Hz (50 Hz), a sync pulse is generated $\frac{1}{120}$ sec ($\frac{1}{100}$ sec) after the previous detection and then the threshold detection scheme 491 is re-enabled to detect the next threshold-cross expected $\frac{1}{120}$ sec ($\frac{1}{100}$ sec) later still. Note the insertion of this sync pulse $\frac{1}{120}$ sec ($\frac{1}{100}$ sec) could optionally be performed after instead of before the signal delay 410.

Now referring back to FIG. 9, with the sync delay then sample calculator 49 applying a series of varying delays to the sync signal 45 events, a series of pulses are then generated by the pulse generator 410. The sample/hold section 420 then samples during a pulse and holds in the absence of a pulse. Pulse duration is set short compared to the duration of the reference cell minimums 411e in order to maintain suitable sample resolution.

Returning to the reference cell signal 411, it is can be first fed into a low pass filter 44 to remove RF and other noise considered high frequency with respect to 120 Hz (100 Hz or pulsed DC) though this filter may not be required as the later moving average filter 430 will also act to remove this noise. Next, the reference cell signal 411 is fed into the sample/hold section 420 which samples when it receives a sync pulse from the sync generator 410 and holds the sample in the absence of this pulse. With a properly computed sync delays 49, the sample/hold section 420 will capture various points along the minimum 411e of the reference cell signal 411 and exclude that portion of the waveform attributed to the leading edge minimum dips 411c and 120 Hz (100 Hz or pulsed DC) IR drop 411b.

Next, the collected sample points are passed through a moving average filter 430 that may be either analog or digital or a combination of both. The moving average filter's 430 parameters are adjusted so the residual 60 Hz (50 Hz) component 411d on the series of collected sample points is removed. Note that in the case where samples are being taken at a 120 Hz (100 Hz) rate, the 60 Hz (50 Hz) residual is necessarily removed by the moving average filter 430 since $Sin(A)=-Sin(A+180)$ and samples will be spaced 180 degrees apart. Also in this case, the slope based minimum hunt routine will not be affected by the residual 60 Hz (50 Hz) as the hunt routine examines averages over a number of cycles. The result is the DC bias 411a present on the reference cell signal is delivered devoid of noise like RF, and components like 120 Hz (100 Hz or pulsed DC) IR drop 411b, small negative dips on the leading edge of minimums 411c, and 60 Hz (50 Hz) residual 411d. This resulting DC bias 411a is correlated with the true reference cell potential and, for practical purposes, is taken as the true reference cell potential.

A specific simple example of an analog Moving Average (low pass) Filter 430 would be a resistor-capacitor network adjusted to take the average output of the sample-hold over numerous cycles.

A specific simple example of a digital moving average filter 430 would be one that takes periodic readings of the sample-hold output, sums them into the moving average of previous samples multiplied by the one minus the sample size, and divides the resulting sum by the samples size. New Average=((Old Average)*(1−Sample Size)+New Sample)/Sample Size. The sample size variable and frequency of sampling is adjusted to take the average output of the sample-hold over numerous cycles.

Figure 11:
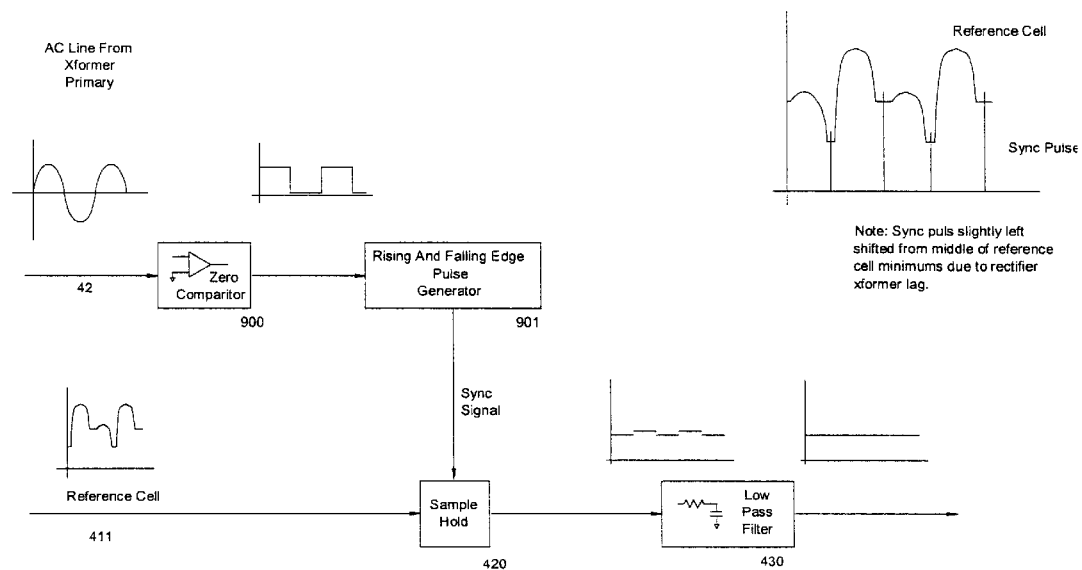
FIG. 11 shows an alternative portable compatible monitor scheme to derive the reference cell potential measurement while impressed current is being applied to the structure, wherein the sample collection window is established in an alternatively simplified manner.

FIG. 11 shows a specific minimalist execution of an integral rectifier/monitor that applies rectified line voltage to the structure by means of step down transformer and diode bridge. A signal is generated from the primary AC line 42 using the prior discussed technique of applying a comparitor 900 to detect when the line signal crosses the zero voltage axis. Each threshold-crossing event produces an edge that the rising and falling edge to pulse generator 901 uses to create pulses that constitute the sync signal. This initial sync signal then has applied a fixed sample start delay 902 to account for phase lag introduced to the reference cell signal by the main rectifier transformer supplying power to the structure. The sync signal is then feed into a sample/hold section 420 that captures and holds a single point at each reference cell minimum. The simplifying assumption here is that when the sync pulse is positioned to occur slightly after (transformer lag) the point where the diode bridge full wave rectified minimums occur, they will hit the reference cell signal minimum right in the middle; after the leading edge dips have died out and before the components from the 120 Hz (100 Hz or pulsed DC) IR drop return. Implicit in this assumption is that the phase of the 60 Hz (50 Hz) residual is not so shifted from the IR drop as to result an unequal spacing between minimums. The output of the sample hold 420 is then averaged by a low pass filter 430 to remove the effects of any residual 60 Hz (50 Hz) along with other noise. The output of the filter is then taken as the true reference cell potential.

Figure 12:
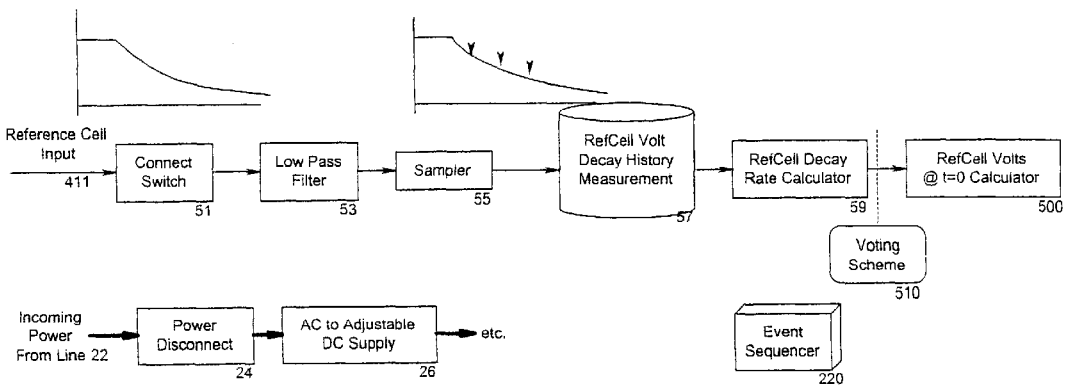
FIG. 12 demonstrates a means for determining what the reference cell potential was immediately before impressed current shutdown.

As seen in FIG. 12, the reference cell shutdown computation 50 provides a means of analyzing the initial decay profile of the reference cell after shutdown (typically on the order of a second or less), extrapolating the reference cell potential decay rate and, in the case of using the method of multiple measurement curve fitting, determining reference cell potential prior to shutdown.

A shutdown is initiated by the event sequencer 220, which first uses the power disconnect 24 to shutdown the adjustable DC supply section that has been providing impressed current to the structure. The event sequencer 220 also begins timing the shutdown action. From a practical standpoint, a voltage transient can be expected on the reference cell signal 411 because of inductive transients generated by disconnecting the adjustable DC supply 27, though this transient can be minimized by disconnecting at a zero-zerocross or minimum power level. Once this inductive has passed, typically well under a second, the event sequencer will close the connect device or contact 51, thereby connecting the reference cell signal 411 to the low pass filter 53.

The signal of interest is the initial decay of the reference cell potential as depolarization of the cathodically protected structure takes place in the absence of impressed current, and relatively rapid signal changes can be considered noise, such as impressed 60 Hz (50 Hz) and harmonics from surrounding power distribution, random signals from other nearby cathodic protection devices, and radio frequencies. The low pass filter 53 is designed to attenuate this noise without distorting the decaying signal of interest.

The sampler 55 takes one or more measurements of the initial decay of the reference cell potential and records these voltage levels along with the time they were taken into the reference cell decay history 57. Typically these readings will be taken within a second of shutdown although adaptive techniques can be employed to dynamically adjust interval duration so that quicker/slower decays will have shorter/longer measurement intervals.

In order to reduce the impact of noise and sampling errors, a given measurement may be comprised of a cluster of samples, and the average sample value (or weighted average sample value for the anticipated non-linear decay profile) is used as the measurement value. The cluster-sample duration must be short enough not to compromise accuracy of a "single point" measurement but ideally long enough to further attenuate anticipated 60 Hz (50 Hz) noise. A cluster sample may be over a multiple of $\frac{1}{60}$ sec, a 60 Hz period, in order to specifically target reduction of 60 Hz noise ($\frac{1}{50}$ sec multiple for 50 Hz noise). A typical cluster sample might be the average of twenty individual samples taken over a $\frac{1}{30}$ sec period (two 60 Hz periods) should the initial reference cell decay profile be slow enough in comparison.

One method the reference cell decay rate calculator 59 can use takes a single measurement $V_{r1}$ (generally comprised of a cluster of samples) at a given length of time after shutdown, typically a second. This measurement is then divided by the reference cell voltage obtained by the continuous monitor just prior to shutdown $V_{r0}$. The result, when subtracted from one, is the percent of reference cell decay over a given time span, again typically a second.

RefCell Decay Rate=$V_{r0}$continuous monitor/$V_{r1}$

Another method the reference cell decay rate calculator 59 can use is to take multiple measurements during the initial reference cell decay and apply curve fitting algorithms to determine a function that is a best-fit for the initial reference cell decay profile voltage and time data. After determining a best-fit-function from among straight-line, exponential, or second order or higher polynomial options, the best-fit-function is then used to extrapolate what the decay profile parameters are for the structure. Furthermore, the reference cell potential at a time just before impressed current shutdown can also be calculated for comparison to the continuous monitor reading.

As a specific application of this general multiple measurement method, the reference cell decay rate calculator 59 is configured to always assume the best-fit-fiction is an exponential decay function. This model has $Vt_1 = Vt_0 e^{(t_1-t_0)/T}$, where $Vt_0$ is the reference cell potential at shutdown 500 or time $t_0$, $V_{r1}$ is voltage at time $t_1$, and T is the time constant tau. This is a capacitive model for initial reference cell decay and is consistent with the actual chemical and physics principles behind structure de-polarization. To simplify applying this model, measurements can be taken at equally spaced time intervals:

since $V_{r1}=V_{r0}\hat{}(t_1-t_0)/T$ and $V_{r2}=V_{r1}\hat{}(t_2-t_1)/T$ then $T=(t_1-t_0)/\ln(V_{r1}/V_{r0})=(t_2-t_1)/\ln(V_{r2}/V_{r1})$, where $T$ is a constant for the profile since $(t_1-t_0)=(t_2-t_1)$ i.e., measurements are taken at equal intervals then $V_{r2}/V_{r1}=(1-\text{RefCell Decay Rate})=$a constant for the initial decay profile$=V_{r1}/V_{r0}$ so $V_{r0}=V_{r1}/(1-\text{RefCell Decay Rate})=$the reference cell potential just before shutdown.

$V_{r0}$ has been extrapolated from $V_{r1}$ and $V_{r2}$, where these later readings were made once the shutdown transients had died out. Note that, as later described, the initial reference cell potential decay rate used to calculate $Vt_0$ is ultimately decided by a voting scheme 60 that typically normalizes the decay rate to that of percent decay after one second.

To afford better noise immunity and to reduce sampling errors, not two, but a series of measurements (each measurement optionally comprised of a cluster-sample) can be made at intervals along the initial reference cell decay profile. Then, a number of decay rate and $V_{t0}$ calculations are made from which average values are calculated. Illustrating using the exponential decay fiction as the best-fit-function:

Set $(t_1-t_0)=(t_2-t_1)=(t_3-t_2)=(t_N-t_{N-1})$

Then 1−RefCell Decay Rate1=$V_{t2}/V_{t1}$
And 1−RefCell Decay Rate2=$V_{t3}/V_{t2}$
And 1−RefCell Decay Rate3=$Vt_4/V_{t3}$
And 1−RefCell Decay RateN=$Vt_N/V_{tN-1}$.
Then RefCell Decay Rate=Avg(RefCell Decay Rate1, . . . RefCell Decay RateN)

Again $(t_1-t_0)=(t_2-t_1)=(t_3-t_2)=(t_N-t_{N-1})$

And $V_{t01}=V_{t1}/(1-\text{RefCell Decay Rate})$

And $V_{t02}=Vt_2/(1-\text{RefCell Decay Rate})^2$

And $V_{t03}=V_{t3}/(1-\text{RefCell Decay Rate})^3$

And $V_{t0N}=V_{tN}/(1-\text{RefCell Decay Rate})^N$

Then $V_{t0}=\text{Avg}(V_{t1}, V_{t2}, V_{t3}, \ldots V_{tN})$

Note again, and as later described, the reference cell decay rate ultimately used to calculate $V_{t01}$, $V_{t0}$, $V_{t03}$, etc. is decided by a voting scheme.

As an alternative method of $V_{t0}$ calculation, if the vote scheme reveals the reference cell decay rate from the above calculations to be within tolerance:

Again $(t_1-t_0)=(t_2-t_1)=(t_3-t_2)=(t_N-t_{N-1})$

And $V_{t01}=V_{t1}^2/V_{t2}$

And $V_{t02}=V_{t2}^3/V_{t3}^2$

And $V_{t03}=V_{t3}^4/V_{t2}^3$

And $V_{t0N}=V_{tN}^{(N+1)}V_{tN-1}^N$

Then $V_{t0}=\text{Avg}(V_{t01}, V_{t02}, V_{t03}, \ldots V_{t0N})$

Figure 13:
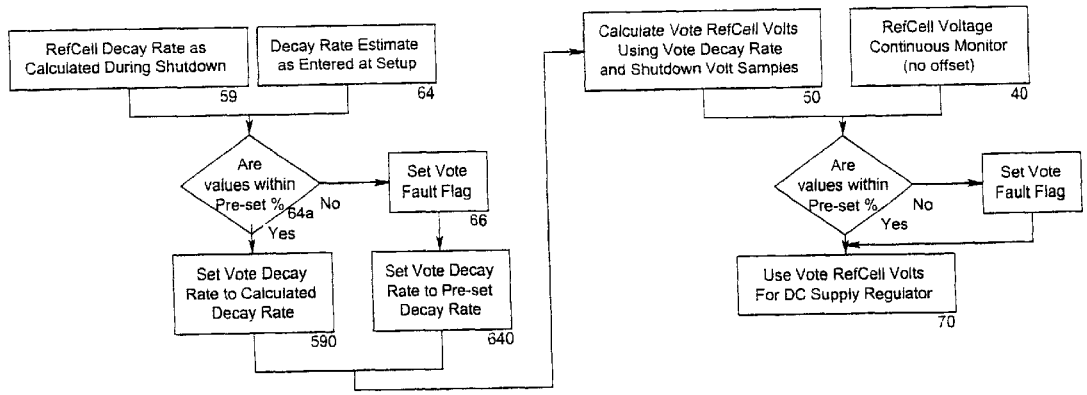
FIG. 13 is a flow diagram showing the reference cell potential vote scheme, which provides a means of cross-checking for improved confidence that the value accepted is true reference cell potential.

Referencing FIG. 13, the reference cell potential vote 60 scheme provides a means of cross-checking in order to improve confidence in the value accepted for true reference cell potential.

During initial cathodic protection device installation, the installers assess the structure being protected and, using conventional measurement techniques and professional judgement, arrive at an estimate of the structure's depolarization decay rate in terms of % Decay/Second. This measurement is a standard benchmark used in the industry. A small structure may decay by 15% in a second whereas a large structure only 2%. This decay estimate 64 is then entered into the memory of the cathodic protection device 10 (FIG. 1) by the installer.

By means outlined in the previous section for the reference cell shutdown computation 50, the shutdown reference cell decay rate 59 has been determined. This value is then compared to the installer's estimate 64 of the reference cell decay rate. If within the pre-set, but field adjustable percentage, typically 5%, the shutdown reference cell decay rate 59 is taken as valid. If not within the percentage, the vote fault flag 66 is set and the installer's estimate 64 (or optionally a moving average of recent past decay rates) of the reference cell decay rate 59 is used for subsequent computations during this shutdown cycle.

Next if the multiple measurement method of decay calculation has been employed, the reference cell potential before shutdown is calculated as outlined in the previous section on reference cell shutdown computation 50. This value is then compared to the value last recorded by the continuous monitor 40 method of reference cell potential. If not within the pre-set but field adjustable percentage the vote fault flag 66 is set. In the absence of a fault, the reference cell potential determined by the continuous monitor is accepted and used for subsequent decisions regarding whether any voltage adjustments will be made by the DC supply regulator to the adjustable DC supply 27 (FIG. 2, 3). In the event of a fault, several options are provided for estimating true reference cell potential including talking the one second decay voltage and estimating voltage at time zero from the installer's estimate of decay rate.

Figure 14:
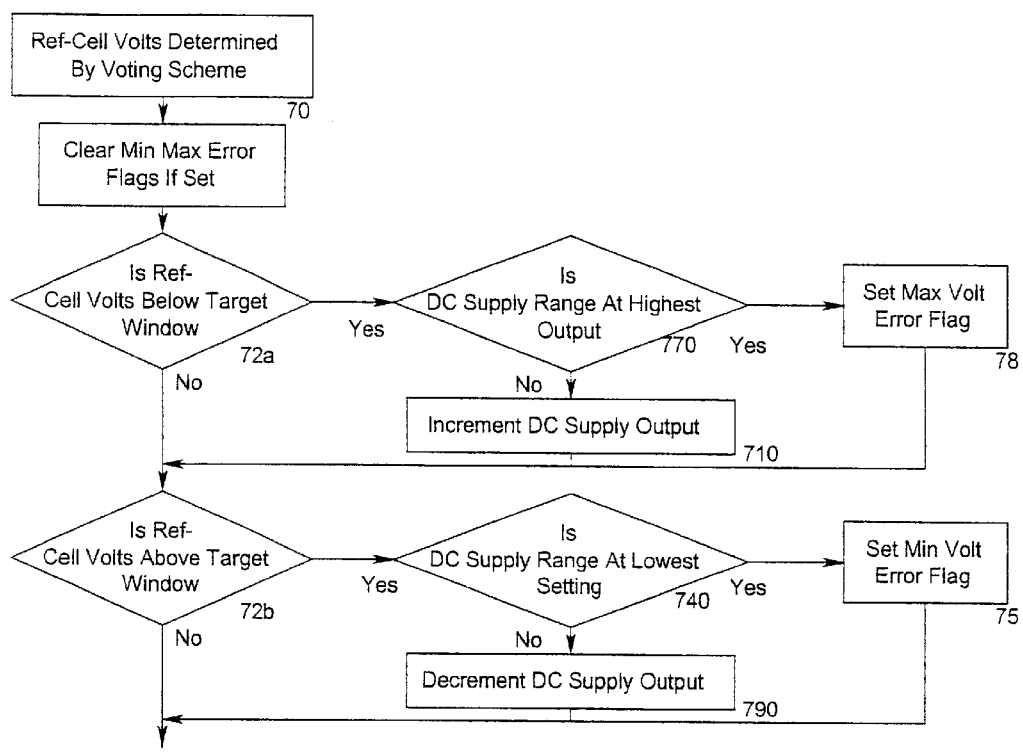
FIG. 14 is a flow diagram showing the adjustable DC supply regulation process when in reference cell mode.

FIG. 14 shows the DC supply regulation section which, when in reference cell mode, provides a means of varying the voltage output of the cathodic protection device 10 in order to satisfy reference cell potential regulation requirements.

Once a true reference cell potential has been determined by the voting scheme 60, that true reference cell potential is compared to a minimum voltage threshold 72a, typically 0.85 volts, and a maximum voltage threshold 72b, typically 1.2 volts. These voltage threshold values are pre-set and, while field adjustable, typically are not changed.

If the true reference cell potential is below the minimum target voltage window 72a, the adjustable DC supply's output 27a is incrementally increased 710, unless it is already at its maximum output 770, in which case the maximum volt error flag is set 78 and the voltage level is left unchanged. If the true reference cell potential is above the maximum target window 72b, adjustable DC supply's output 27a is incrementally decreased 790, unless it is already at its minimum output 740, in which case the minimum volt error flag is set 75 and the voltage level is left unchanged.

Note that the adjustable DC supply 27 is being regulated within the field set voltage window that establishes the overall maximum and minimum voltage levels the adjustable DC supply 27 is allowed to deliver. This window exists so that if there was a logic error, damaging excessive voltage (or pulsed DC) can not be passed to the structure, nor would there be an absence of voltage (or pulsed DC) being passed to the structure leaving it vulnerable. Regular occurrence of a minimum volt error flag 75 or maximum volt error flag 78 indicates a need to adjust the thresholds of this window.

Figure 15:
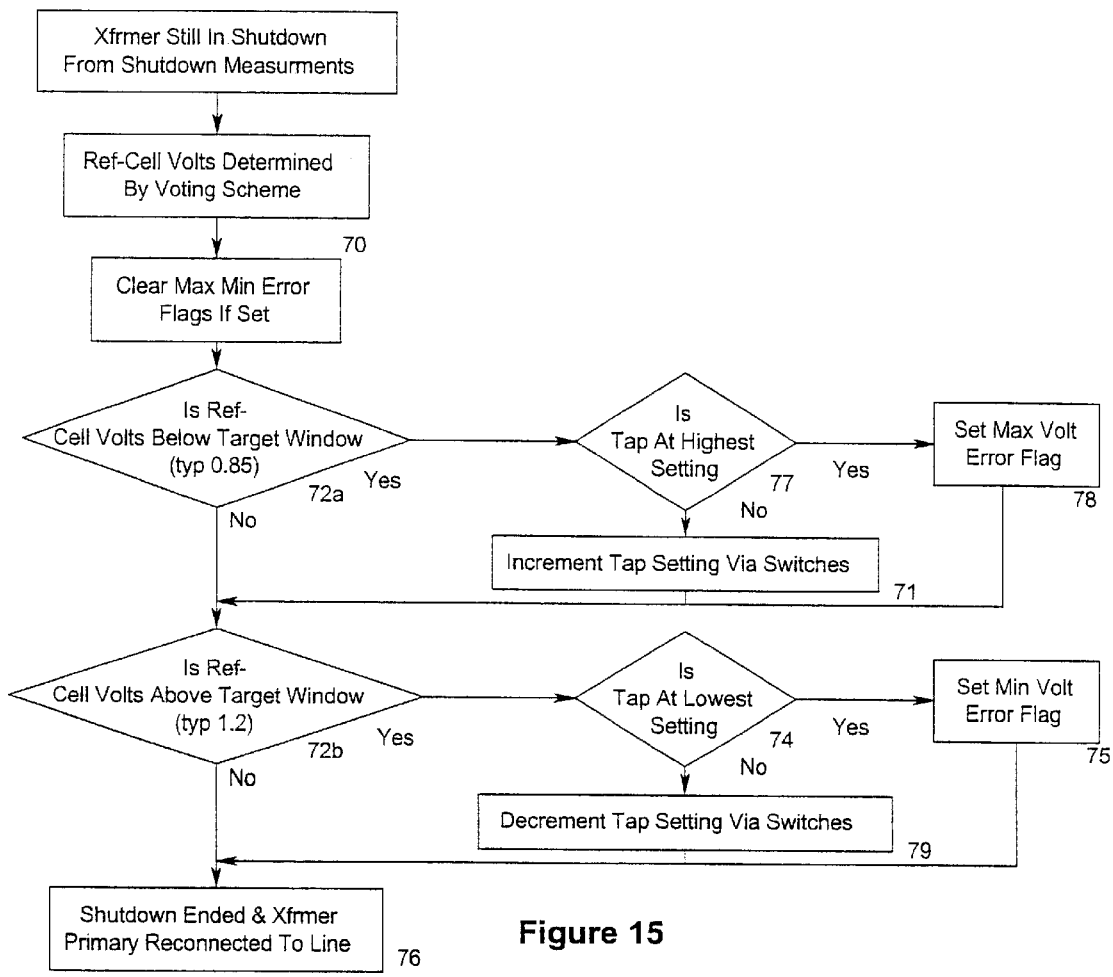
FIG. 15 is a flow diagram showing the adjustable DC supply regulation process using tap regulation when in reference cell mode.

FIG. 15 shows the adjustable DC supply 27 (FIG. 2, 3) which, when in reference cell mode, provides a means of changing the fine taps on the selectable tap transformer 26 in order to vary the voltage output of the cathodic protection device 10 in order to satisfy reference cell potential regulation requirements.

Once a true reference cell potential has been determined by the voting scheme 70, that true reference cell potential is compared to the minimum voltage threshold, typically 0.85 volts, and the maximum voltage threshold, typically 1.2 volts.

If the true reference cell potential is below the minimum target voltage window 72a, the selectable tap transformer is moved up a tap 71, unless it is already at the top tap 77, in which case the maximum volt error flag is set 78 and the tap is left unchanged. If the true reference cell potential is above the maximum target voltage window 72b, the selectable tap transformer is moved down a tap 79, unless it is already at the bottom tap setting 74, in which case the minimum volt error flag is set 75 and the tap is left unchanged.

Note that when the tap regulation section acts to switch the selectable tap transformer's secondary taps, the selectable tap transformer's primary is first disconnected from incoming line 22. This is done so that the secondary taps, with their lower voltage but higher current configuration, are not switched under load. Once switching is complete, power from AC line 22 is restored to the selectable tap transformer 26.

When in reference cell mode, tap switching events can be placed immediately after the reference cell potential vote action. This way the selectable tap transformer 26 is already disconnected from AC line 22 power as a result of a shutdown and disconnect cycles can be reduced. Once switching is complete, AC line 22 power is restored to the selectable tap transformer 26.

Figure 16:
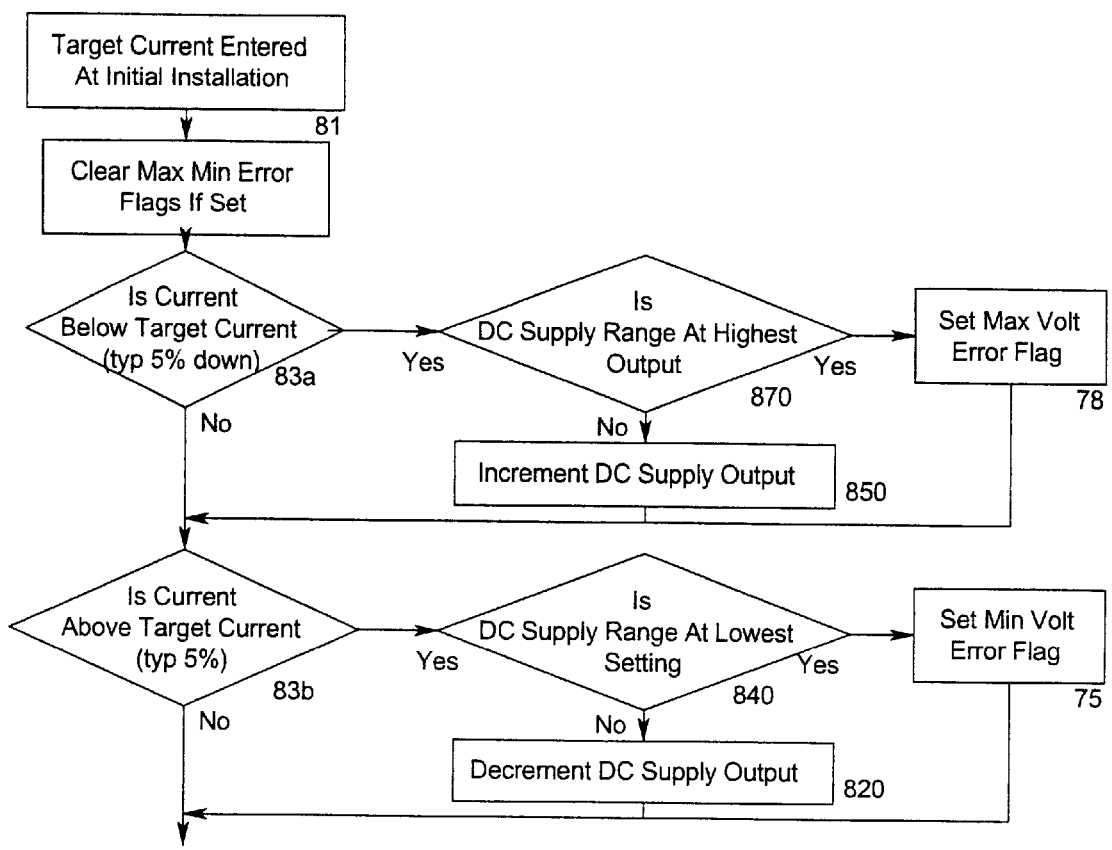
FIG. 16 is a flow diagram showing the adjustable DC supply regulation process when in current mode.

FIG. 16, shows the DC supply regulation section which, when in current mode, provides a means varying the voltage and therefore current output of the cathodic protection device 10 in order to satisfy current regulation requirements to the structure 2.

The current being delivered to the structure 2 is compared to the minimum current threshold 83a, typically 5% below the desired target current, and the maximum current threshold 83b, typically 5% above the target current. Though the percent of deviation allowed is pre-set to 5%, it is field adjustable. Target current level 81 is typically recorded at the time of installation, though it may be changed later, and can either be manually set, or it can be automatically and/or remotely set by having the controller memorize the amount of current being delivered to the structure at the moment of the automatic set request.

If the current is below the minimum target current 81, 83a, adjustable DC supply 27 is incrementally increased 850, unless it is already at its maximum output 870, in which case the maximum volt error flag 78 is set and the voltage level 27a is left unchanged. If the current is above the maximum target current 81, the adjustable DC supply 27 is incrementally decreased 820, unless it is already at its minimum output 840, in which case the minimum volt error flag 75 is set and the voltage level 27a is left unchanged.

As in FIG. 14, the adjustable DC supply 27 (FIG. 2, 3) is being regulated within the field set voltage window that establishes the overall maximum and minimum voltage, and thus current levels the adjustable DC supply 27 is allowed to deliver.

Figure 17:
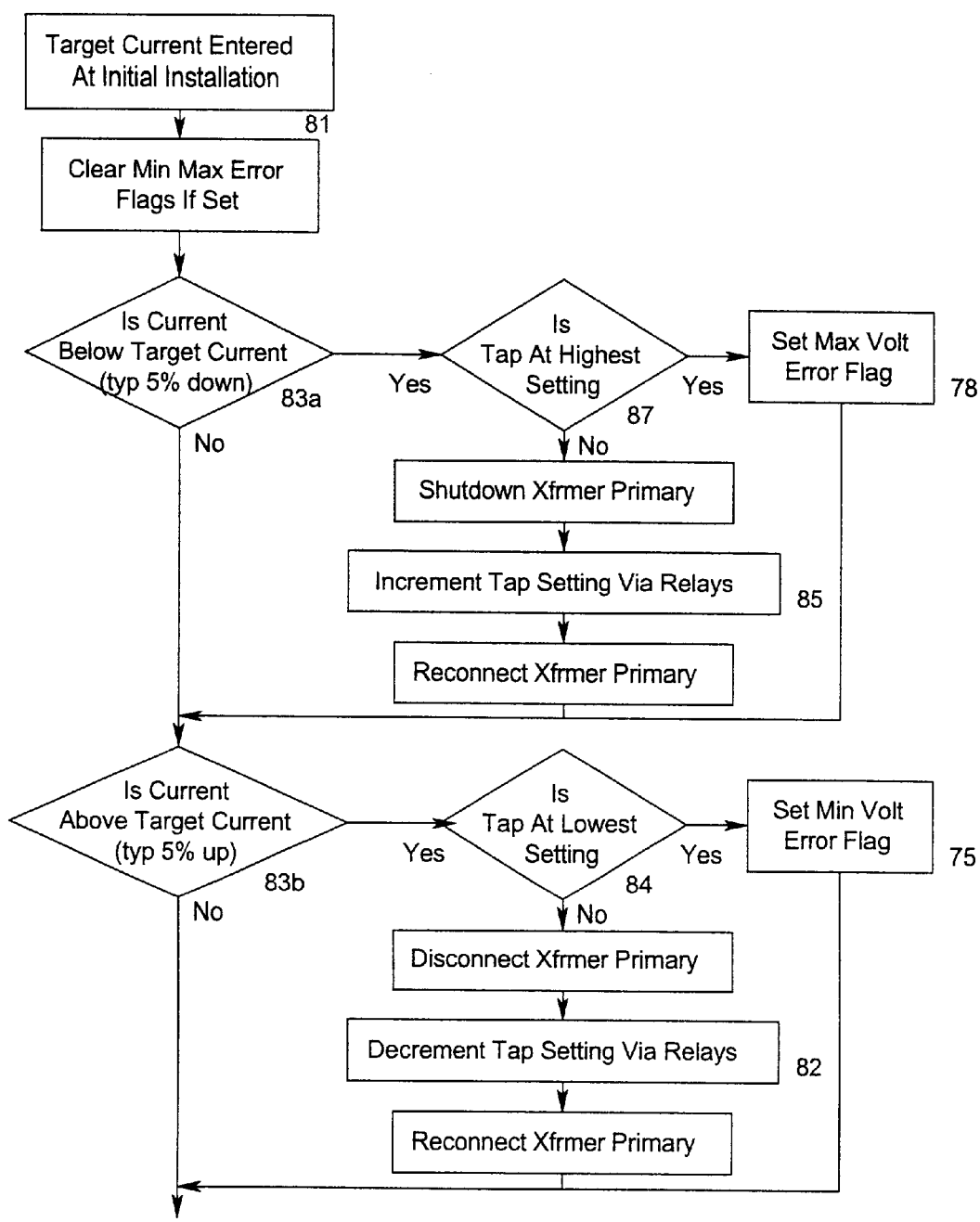
FIG. 17 is a flow diagram showing the adjustable DC supply regulation process using tap regulation when in current mode.

FIG. 17 shows the adjustable DC supply 27 (FIG. 2, 3) which, when in current mode, provides a means of changing the fine taps on the selectable tap transformer 26 in order to vary the voltage and therefore current output of the cathodic protection device 10 in order to satisfy current regulation requirements.

The current being delivered to the structure 2 is compared to the minimum current threshold 83a, typically 5% below the desired target current, and the maximum current threshold 83b, typically 5% above the target current. Though the percent of deviation allowed is initially set to 5%, it is field adjustable.

If the current is below the minimum target current 83a, the selectable tap transformer is moved up a tap 85, unless it is already at the top tap 87, in which case the maximum tap error flag is set 78 and the tap is left unchanged. If the current is above the maximum, the selectable tap transformer 26 is moved down a tap 82, unless it is already at the bottom tap 84, in which case the minimum tap error flag is set 75 and the tap is left unchanged. Again, it should be understood that when the tap regulation section acts to switch the selectable tap transformer's secondary taps, the selectable tap transformer's primary is first disconnected from AC line 22. This is done so that the secondary taps, with their lower voltage but higher current configuration, are not switched under load. Once switching is complete, incoming power is restored to the selectable tap transformer.

When in current mode, a shutdown is not required to attain a measurement of the current being delivered to the structure 2, so, the selectable tap transformer 26 has not been, and must be, disconnected from incoming power for a tap switching event, then reconnected upon completion.

FIG. 18 shows detail of the transformer tap controller 28 (FIG. 2a, 3a). The transformer tap controller is configured in such a way as to ensure that if none of its switching devices are energized, it will still output a voltage corresponding to the lowest fine tap setting. The transformer tap controller 28 is also configured to prevent accidental shorting of selectable tap transformer's 26 secondary taps regardless of the state of the switching devices.

FIG. 9 shows 5 switching devices S1, S2, S3, S4, and SN, though there may be more or less depending on the number of fine taps to be regulated, and it shows the switching devices as relay contacts, though they could be IGBT, transistors, MOSFETs or other switching devices. For illustrative purposes, three course taps are also shown and the middle one selected but again, there may be more or less course taps depending on the selectable tap transformer. Also, in contrast to how the taps are shown here, taps on the selectable transformer may be arranged to provide overlap between course and fine tap voltage selection. That is, fine tap movement within a course tap setting may output voltages that overlap fine tap movements over adjacent course tap settings.

To output the lowest available voltage for a given course tap setting, S1, S2, S3, S4, and Sn are left in their default state as shown. S1, when un-energized, defaults to selection of fine tap #1. This is an added measure of safety to ensure that should the switching device drivers of the tap controller fail, the structure will still receive a minimal level of cathodic protection.

To incrementally increase the selectable tap transformer voltage, S1 and S2 are energized thereby disconnecting fine tap #1 and engaging fine tap #2. To step voltage up more, S1 and S3 are energized thereby disconnecting fine tap #2 and engaging fine tap #3. Maintaining S1 and energizing S4, then Sn, etc. will correspondingly engage fine tap #4, fine tap #n, etc. and correspondingly increment the selectable tap transformer 26 (2a, 3a) voltage output more.

Note that in this configuration, random energizing of S1, S2, S3, S4, and Sn will not cause fine taps to be shorted to one another. The tap controller 28 (FIGS. 2a, 3a) is configured in a cascading fashion such that as each switching device is energized, which incrementally increases voltage output, as each previous switching device is removed from the circuit (with the exception of S1 which is configured so a minimum voltage is always delivered to the structure 2).

We claim:

1. A method for regulating output and continuously and remotely monitoring measurements of reference cell potential or current for cathodic protection of a structure, comprising:

providing one or more cathodic protection devices located proximate to said structure to vary said output;

piggybacking an internal interface unit accessible by a central computer on each of said cathodic protection devices;

communicating with each of said cathodic protection devices by means of said internal interface unit;

providing and displaying said measurements to said central computer;

comparing and cross-checking said measurements using a voting scheme, thereby improving confidence in said measurements;

varying said output being applied to said structure as determined by said voting scheme such that said measurements fall within a target window; and removing distorting effects, residual components, and noise from said measurements to arrive at an amplitude for a DC bias, wherein said amplitude for said DC bias is correlated to said reference cell potential.

2. The method of claim 1, wherein said output is an adjustable DC supply for regulating said reference cell potential.

3. The method of claim 1, wherein said output is an adjustable DC supply for regulating said current.

4. The method of claim 1, wherein said measurements are provided and displayed using the Internet.

5. The method of claim 1, wherein said measurements are provided and displayed using a cellular phone.

6. The method of claim 1, wherein said measurements are provided and displayed using said central computer.

7. The method of claim 1, wherein said measurements are provided and displayed using a radio.

8. A system for regulating output and continuously and remotely monitoring measurements of reference cell potential or current for cathodic protection of a structure, comprising:

one or more cathodic protection devices adapted to function in reference cell mode or current mode and located proximate to said structure to vary said output;

an internal interface unit accessible by a central computer and piggybacked on each of said cathodic protection devices;

a central station running said central computer and communicating with each of said cathodic protection devices by means of said internal interface unit;

a voltage detection means working in conjunction with said cathodic protection device providing and displaying said measurements to said central computer, wherein said voltage detection means comprises a low pass filtered output voltage of a current sense device;

a voting scheme means for comparing and cross-checking said measurements, thereby improving confidence in said measurements; and, a regulation means for varying said output as determined by said voting scheme.

9. The system of claim 8, wherein said current sense device is a hall effect device.

10. The system of claim 8, wherein said current sense device is a shunt.

11. The system of claim 8, wherein said current sense device is a current sense resistor placed in series with power flow.

12. The system of claim 8, wherein said regulation means comprises an adjustable DC supply controllable by a shut-down controller under logic sequence control.

13. The system of claim 12, wherein said adjustable DC supply comprises course upper and lower limits that define an adjustment window, and further comprises fine taps set within said adjustment window.

14. The system of claim 8, wherein said regulation means comprises a transformer tap controller connected by a series of switching devices to a selectable tap transformer.

15. The system of claim 14, wherein said transformer tap controller is configured to output a voltage corresponding to a lowest tap setting when none of said switching devices are energized.

16. The system of claim 8, wherein said internal interface unit is accessible over the Internet.

17. The system of claim 8, wherein said internal interface unit is password protected.

18. In a system for regulating output and continuously and remotely monitoring measurements of reference cell potential or current for cathodic protection of a structure, a reference cell continuous monitor, comprising:

a means for removing noise, distorting effects, and residual components from said system, thereby producing a value for a true reference cell potential, wherein said value is provided regardless of whether or not said system has been shutdown.

19. The reference cell continuous monitor of claim 18, wherein said distorting effect is an IR drop.

20. The reference cell continuous monitor of claim 19, wherein said IR drop is a varying DC component from a full wave rectified line frequency being applied to said structure.

21. The reference cell continuous monitor of claim 18, wherein said noise is a component that appears as small negative approaching dips on leading edges of reference cell signal minimums.

22. The reference cell continuous monitor of claim 18, wherein said residual component is an un-rectified residual component of arbitrary phase delay.

23. The reference cell continuous monitor of claim 22, wherein said un-rectified residual component originates from a surrounding power grid.

24. A method for regulating output and continuously and remotely monitoring measurements of reference cell potential or current for cathodic protection of a structure, comprising:

providing one or more cathodic protection devices located proximate to said structure adapted to vary said output;

communicating with each of said cathodic protection devices using a central computer to remotely configuring each of said cathodic protection devices with a plurality of parameters, wherein each of said cathodic protection devices is queried at user set intervals; and, interfacing each of said cathodic protection devices with the Internet such that an operational history of each of said cathodic protection devices is available by way of an internet addressing scheme.

25. The method of claim 24, wherein one of said parameters includes how said current is being applied.

26. The method of claim 24, wherein one of said parameters includes a time constant for a shut-down decay rate.

27. The method of claim 24, wherein one of said parameters includes periodic shut-down cycle time intervals.

28. The method of claim 24, wherein one of said parameters includes adjustable limits for said output, wherein said output is an adjustable DC supply.

29. The method of claim 24, wherein one of said parameters includes a selection of event data logging.

30. The method of claim 24, wherein one of said parameters includes a variety of selectable control and annunciation schemes.

31. The method of claim 24, wherein for the step of communicating with each of said cathodic protection devices, a simultaneous shutdown of all of said rectifiers and controllers is coordinated.

32. The method of claim 24, wherein said operational history is password accessed.

33. In a system for regulating output and continuously and remotely monitoring measurements of reference cell potential or current for cathodic protection of a structure, a method for arriving at and regulating said reference cell potential, comprising the steps of:

providing a continuous monitor to remove distorting effects, residual components, and noise from said system to arrive at an amplitude for a DC bias;

correlating said DC bias with said reference cell potential;

initiating and timing a shutdown of said system to produce a decaying reference cell potential and a shutdown value;

providing a sampler to take a series of measurements of said decaying reference cell potential to produce a reference cell decay rate;

comparing said reference cell decay rate with a decay rate estimate;

comparing said shutdown value with said reference cell potential; and, utilizing a voting scheme to increment or decrement a DC supply or tap setting.

34. The method of claim 33, further comprising the step of providing a reference cell decay rate calculator utilizing curve fitting algorithms to determine said shutdown value.

35. A method for arriving at a true reference cell potential measurement devoid of noise, distorting effects, and residual components, comprising:

generating a sync signal;

establishing a sample collection window for said sync signal, wherein sample points of a reference cell signal are captured along minimums of said reference cell signal;

measuring said reference cell signal within said sample collection window, wherein said sample points of said reference cell signal are devoid of distorting effects and small, negative approaching dips on leading edges of said minimums;

passing said sample points through a moving average filter such that a residual line frequency component of each of said sample points is removed, thereby forming a DC bias of said reference cell signal; and, correlating said DC bias to said true reference cell potential measurement.

36. The method of claim 35, further comprising the step of comparing said true reference cell potential measurement to a measurement of a reference cell potential determined using a calculated shutdown.

37. The method of claim 35, wherein for the step of generating a sync signal, a slope transition event is detected on said reference cell signal.

38. The method of claim 35, wherein for the step of generating a sync signal, all DC components from a duplicated reference cell signal are removed.

39. The method of claim 35, wherein for the step of generating a sync signal, a non-rectified AC line reference signal is analyzed.

40. The method of claim 39, wherein said AC line reference signal is stripped of any DC component.

41. The method of claim 35, further comprising the step of applying a delay to said sync signal.

42. The method of claim 41, wherein said delay is applied by determining a midway point on at least one of said minimums of said reference cell signal.

43. The method of claim 42, wherein said midway point is determined by determining a width of a waveform of said reference cell signal when said waveform crosses a voltage threshold.

44. The method of claim 35, wherein said sample collection window is adjustable to establish bounds for each a sample start delay and a sample end delay.

45. The method of claim 44, wherein said sample start delay is positioned after each of said small, negative approaching dips.

46. The method of claim 44, wherein said sample start delay is positioned before distorting effects of an IR drop component.

47. The method of claim 44, wherein said sample start delay is positioned to account for a phase lag introduced to said reference cell signal by a rectifier transformer supplying power to a structure.

48. The method of claim 35, wherein the step of measuring said reference cell signal further comprises the steps of:

generating a series of pulses;

feeding said reference cell signal into a sample and hold section, wherein
said sample points are captured during each of said pulses.

49. The method of claim 35, wherein before the step of passing said sample points through said moving average filter, said reference cell signal is fed into a low pass filter to remove RF and other noise considered high frequency.

50. The method of claim 35, wherein said moving average filter is digital.

51. The method of claim 35, wherein said moving average filter is analog.

52. The method of claim 35, wherein said residual line frequency component is 60 Hz.

53. The method of claim 35, wherein said residual line frequency component is 50 Hz.

54. The method of claim 35, wherein said residual line frequency component is pulsed DC.

* * * * *